US011708395B2

(12) United States Patent
Zhang et al.

(10) Patent No.: US 11,708,395 B2
(45) Date of Patent: Jul. 25, 2023

(54) GENE LBA5 FOR REGULATING LATERAL SHOOT ANGLES, GROWTH HABITS, AND PLANT ARCHITECTURE OF *ARACHIS HYPOGAEA* L., AND USE THEREOF

(71) Applicant: Qingdao Agricultural University, Qingdao (CN)

(72) Inventors: Xiaojun Zhang, Qingdao (CN); Fanzhuang Yan, Qingdao (CN); Xiaona Yu, Qingdao (CN); Shaojing Zhang, Qingdao (CN); Tong Si, Qingdao (CN); Xiaoxia Zou, Qingdao (CN); Yuefu Wang, Qingdao (CN); Minglun Wang, Qingdao (CN)

(73) Assignee: Qingdao Agricultural University, Qingdao (CN)

( * ) Notice: Subject to any disclaimer, the term of this patent is extended or adjusted under 35 U.S.C. 154(b) by 0 days.

(21) Appl. No.: 17/617,602

(22) PCT Filed: Oct. 12, 2020

(86) PCT No.: PCT/CN2020/120312
§ 371 (c)(1),
(2) Date: Dec. 9, 2021

(87) PCT Pub. No.: WO2021/073466
PCT Pub. Date: Apr. 22, 2021

(65) Prior Publication Data

US 2022/0227821 A1 Jul. 21, 2022

(30) Foreign Application Priority Data

Oct. 18, 2019 (CN) ......................... 201910994923.6

(51) Int. Cl.
*C12N 15/113* (2010.01)
*C07K 14/415* (2006.01)
*C12N 15/82* (2006.01)

(52) U.S. Cl.
CPC .......... *C07K 14/415* (2013.01); *C12N 15/113* (2013.01); *C12N 15/8218* (2013.01); *C12N 15/8262* (2013.01); *C12N 2310/20* (2017.05)

(58) Field of Classification Search
None
See application file for complete search history.

(56) References Cited

FOREIGN PATENT DOCUMENTS

| | | | |
|---|---|---|---|
| CN | 110592102 | A | 12/2019 |
| WO | 03000862 | A2 | 1/2003 |
| WO | 2013012889 | A2 | 1/2013 |
| WO | 2018022574 | A2 | 2/2018 |

OTHER PUBLICATIONS

Matthews et al. “Marker gene elimination from transgenic barley, using co-transformation with adjacent ‘twin T-DNAs’ on a standard Agrobacterium transformation vector”. Molecular Breeding. 7: 195-202. (Year: 2001).*

Dorca-Fornell, et al. “The *Arabidopsis* SOC1-like genes AGL42, AGL71 and AGL72 promote flowering in the shoot apical and axillary meristems”. The Plant Journal. 67(6):1006-1017. (Year: 2011).*

Genbank locus XM_025800920 (Year: 2019).*

Sinharoy et al. “Transformed Hairy Roots of Arachis hypogea: A Tool for Studying Root Nodule Symbiosis in a Non-Infection Thread Legume of the Aeschynomeneae Tribe”. Molecular Plant-Microbe Interactions. 22(2):132-142. (Year: 2009).*

Locus CP030997s13. Zhuang,W., Chen,H., Varshney,R., Wang,D. and Ming,R. Genembl Direct Submission. State Key Laboratory of Ecological Pest Control for Fujian and Taiwan Crops, Fujian Agriculture and Forestry University; ICRISAT. (Year: 2018).*

Jiang Jian-Hua, et al., Genetic Analysis of 4 Main Agronomic Traits in Peanut (*Arachis hypogaea* L.), Journal of Peanut Science, 2015, pp. 7-13, vol. 44, No. 3.

XP_015967280.1, MADS-box protein AGL42-like [*Arachis duranensis*], GenBank, 2017.

XM_029293180.1, Predicted: *Arachis hypogaea* MADS-box protein AGL42 (LOC112751701), transcript variant X2, mRNA,GenBank, 2019.

XM_025800920.2, Predicted: *Arachis hypogaea* MADS-box protein AGL42 (LOC112751701), transcript variant X3, mRNA,GenBank, 2019.

XM_029293179.1, Predicted: *Arachis hypogaea* MADS-box protein AGL42 (LOC112751701), transcript variant X1, mRNA,GenBank, 2019.

XM_021103191.1, Predicted: *Arachis ipaensis* MADS-box protein AGL42 (LOC107642209), transcript variant X3, mRNA, GenBank, 2017.

Suruchi Roychoudhry, et al., Shoot and root branch growth angle control—the wonderfulness of lateralness, Current Opinion in Plant Biology, 2015, pp. 124-131, vol. 23.

J. Digby, et al., The gravitropic set-point angle (GSA): the identification of an important developmentally controlled variable governing plant architecture*, Plant, Cell and Environment, 1995, pp. 1434-1440, vol. 18.

(Continued)

*Primary Examiner* — Matthew R Keogh
*Assistant Examiner* — David R Byrnes
(74) *Attorney, Agent, or Firm* — Bayramoglu Law Offices LLC

(57) ABSTRACT

A gene LBA5 for regulating lateral shoot angles, growth habits, and a plant architecture of *Arachis hypogaea* L., and use thereof are provided. In the present disclosure, a major gene LBA5 for controlling lateral shoot angles, growth habits, and a plant architecture of *Arachis hypogaea* L. is mapped and cloned from *Arachis hypogaea* L., which includes two homologous genes LBA5b and LBA5a and promoters thereof. The allelic variations of the gene can be selected through crossbreeding and backcrossing to achieve the genetic improvement on an angle between an *Arachis hypogaea* L. lateral shoot and a main stem. Through a genetic engineering operation for the gene and a change for a promoter sequence of the gene, the function or expression level of this gene in a procumbent *Arachis hypogaea* L. variety can be adjusted to further regulate an angle between an *Arachis hypogaea* L. lateral shoot and a main stem.

5 Claims, 3 Drawing Sheets

Specification includes a Sequence Listing.

(56) References Cited

OTHER PUBLICATIONS

Suruchi Roychoudhry, et al., Auxin Controls Gravitropic Setpoint Angle in Higher Plant Lateral Branches, Current Biology, 2013, pp. 1497-1504, vol. 23, No. 15.

Dayong Cui, et al., The *Arabidopsis* IDD14, IDD15, and IDD16 Cooperatively Regulate Lateral Organ Morphogenesis and Gravitropism by Promoting Auxin Biosynthesis and Transport, PLOS Genetics, 2013, pp. 1-15, vol. 9, Issue 9, e1003759.

Peijin Li, et al., LAZY1 controls rice shoot gravitropism through regulating polar auxin transport, Cell Research, 2007, pp. 402-410, vol. 17.

Zhaobin Dong, et al., Maize LAZY1 Mediates Shoot Gravitropism and Inflorescence Development through Regulating Auxin Transport, Auxin Signaling, and Light Responsel [C][W], Plant Physiology, 2013, pp. 1306-1322, vol. 163.

Fang Bai, et al., TCP transcription factor, Branch Angle Defective 1 (BAD1), is required for normal tassel branch angle formation in maize, PNAS, 2012, pp. 12225-12230, vol. 109, No. 30.

Baisheng Yu, et al., TAC1, a major quantitative trait locus controlling tiller angle in rice, The Plant Journal, 2007, pp. 1-8.

Hua Zhao, et al., Natural variation and genetic analysis of the tiller angle gene MsTACI in Miscanthus sinensis, Planta, 2014, pp. 161-175, vol. 240.

Jian Jin, et al., Genetic control of rice plant architecture under domestication, Nature Genetics, 2008, pp. 1-5.

Lubin Tan, et al., Control of a key transition from prostrate to erect growth in rice domestication, Nature Genetics, 2008, pp. 1-5.

Dajun Sang, et al., Strigolactones regulate rice tiller angle by attenuating shoot gravitropism through inhibiting auxin biosynthesis, PNAS, 2014, pp. 11199-11204, vol. 111, No. 30.

Jia Liu, et al., Characterizing Variation of Branch Angle and Genome-Wide Association Mapping in Rapesee (*Brassica napus* L.), Frontiers in Plant Science, 2016, pp. 1-10, vol. 7, No. 21.

Chengming Sun, et al., Genome-Wide Association Study Dissecting the Genetic Architecture Underlying the Branch Angle Trait in Rapeseed (*Brassica napus* L.), Scientific Reports, 2016, pp. 1-11, 6:33673.

Hui Wang, et al., Identification of BnaYUCCA6 as a candidate gene for branch angle in *Brassica napus* by QTL-seq, Scientific Reports, 2016, pp. 1-10, 6:38493.

Guillermo Seijo, et al., Genomic Relationships Between the Cultivated Peanut (*Arachis hypogaea, leguminosae*) and its Close Relatives Revealed by Double Gish1, American Journal of Botany, 2007, pp. 1963-1971, vol. 94, No. 12.

C. Balaian, et al., Genic analysis in groundnut, Proc. Indian Acad. Sci., 1977, pp. 340-350, vol. 85 B, No. 5.

Fu Jiang, et al., Preliminary Observation on Genetic Variation of Several Main Characters in Peanut, 1984, pp. 9-13, China Academic Journal Electronic Publishing House.

Xinmin Gan, et al., The Genetic Variation of Peanut Individual Quality Traits, 1984, pp. 8-9, China Academic Journal Electronic Publishing House.

Galya Kayam, et al., Fine-Mapping the Branching Habit Trait in Cultivated Peanut by Combining Bulked Segregant Analysis and High-Throughput Sequencing, Frontiers in Plant Science, 2017, pp. 1-11, vol. 8, No. 467.

* cited by examiner

PF group analysis ΔSNP-index

*LBA5b* 1 μl template

*LBA5a* 4 μl template

Actin internal reference

ABC: three upright varieties

DEF: three procumbent varieties

GENE LBA5 FOR REGULATING LATERAL SHOOT ANGLES, GROWTH HABITS, AND PLANT ARCHITECTURE OF *ARACHIS HYPOGAEA* L., AND USE THEREOF

CROSS REFERENCE TO THE RELATED APPLICATIONS

This application is the national phase entry of International Application No. PCT/CN2020/120312, filed on Oct. 12, 2020, which is based upon and claims priority to Chinese Patent Application No. 201910994923.6, filed on Oct. 18, 2019, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBQDGX003-PKG_Sequence Listing.txt, created on 12/05/2021 and is 98,856 bytes in size.

TECHNICAL FIELD

The present disclosure belongs to the field of plant biotechnology and plant genetic engineering, and relates to a plant architecture gene LBA5 for regulating lateral shoot angles and growth habits of *Arachis hypogaea* L., and use thereof. In the present disclosure, the gene LBA5 and a homologous gene thereof are used to conduct biotechnological modification or genetic improvement on a plant architecture of *Arachis hypogaea* L. or other crop.

BACKGROUND

Growth angles of lateral shoots of a plant determine the plant architecture of the entire plant. For most plants, lateral shoots are generally non-vertical, which is convenient for the acquisition of more sunlight, air, and other resources in a population. There have been abundant studies on the genetic control of lateral shoot angles in model plants (Roychoudhry and Kepinski 2015). In the early days, there have been studies to distinguish the gravitropic set-point angle (GSA) determined by gravity from the geotropic growth (Digby and Firn 1995). Gravitropism-determined lateral shoot angle is regulated by the asymmetrical distribution of auxin. The regulation of an auxin synthesis-related gene and a signaling pathway thereof TIR1/AFB-Aux/IAA-ARF for lateral shoot angle has been explained in detail (Roychoudhry, Delbianco et al., 2013). In addition, a number of related genes in *Arabidopsis thaliana* (*A. thaliana*) have been discovered and verified through mutants and other means, including three transcription factors IDD14, IDD15, and IDD16, which coordinate and control the synthesis and transport of auxin. The inactivation of IDD15 can significantly increase an angle between a lateral shoot and a vertical direction (Dayong, Jingbo et al., 2013). In addition to those in the model plant *A. thaliana*, a number of genes for controlling a lateral shoot angle or a tiller angle have been obtained in various other crops through forward genetics. In *Oryza sativa* L., an *Oryza sativa* L. scattering gene LAZY1 is finely mapped and cloned using an $F_2$ population that is constructed by backcrossing a mutant of a scattering plant with an upright-growing *Oryza sativa* L. variety multiple times to obtain an introgression line la1-ZF802 and crossbreeding the introgression line la1-ZF802 with various common *Oryza sativa* L. varieties. This gene is a specific gene in a monocotyledonous herb and plays a negative regulatory role in the polar transport of auxin. Under the background of a defunctionalized lazy1 gene, the polar transport of auxin is enhanced and the gravitropism of tillers is reduced, which in turn leads to an increased tiller angle (Li, Wang et al. 2007). A locus whose corresponding functional gene has a similar function to a homologous gene ZmLAZY1 of the *Oryza sativa* L. LAZY1 is also found in the map-based cloning of tiller angles in *Zea mays* L. (Zhaobin, Chuan et al. 2013). A gene BAD1 for controlling a shoot angle of a stamen has also been discovered in *Zea mays* L., which is a TCP transcription factor that plays a role in the formation of a pulvinus at a base of a lateral shoot (Fang, Renata et al. 2012). TAC1 is another major quantitative trait locus (QTL) for controlling a tiller angle in *Oryza sativa* L. The decrease in TAC1 expression can make *Oryza sativa* L. tillers grow nearly vertically, which plays an important role in the dense planting of *Oryza sativa japonica* in high latitude areas (Yu, Lin et al. 2007). In addition, a homologous gene of TAC1 plays a similar role in the monocotyledonous herb *Miscanthus* (Zhao, Huai et al. 2014). A major QTL PROG for controlling an *Oryza sativa* L. tiller angle has also been found in the genetic mapping for the plant architecture difference between procumbent wild *Oryza sativa* L. and cultivated *Oryza sativa* L., which is a key locus for the domestication of procumbent wild *Oryza sativa* L. into upright cultivated *Oryza sativa* L. and encodes the C2H2 zinc-finger protein (ZNF). Defunctionalized prog1 can make *Oryza sativa* L. change to upright growth from procumbent growth (Jin, Huang et al. 2008, Tan, Li, et al. 2008). As a newly discovered plant endogenous hormone, strigolactone (SL) also plays an important role in the regulation of lateral shoot angle. A mutant sols of a gene for synthesizing SL can inhibit the geotropism of *Oryza sativa* L. tillers by reducing the synthesis of auxin, thereby partially restoring the loose plant architecture of the lazy1 mutant (Dajun, Dongqin et al. 2014). In recent research on the lateral shoot angle in *Brassica napus* L., various loci for controlling a lateral shoot angle have also been found through association analysis and linkage group mapping (Liu, Wang et al. 2016, Sun, Wang et al. 2016). A candidate gene BnaYUCCA6 is mapped by the strategy of extreme population and key region linkage mapping, which is a key gene in the auxin synthesis pathway according to function prediction. There are multiple SNP differences among materials with different lateral shoot angles, which is inferred to be caused by the differential expression of the gene in further research (Hui, Cheng et al. 2016).

Cultivated *Arachis hypogaea* L. is obtained from domestication of a species obtained by subjecting two procumbent wild diploid *Oryza sativa* L. species with different genomes to natural outcrossing and chromosome doubling, and it is generally believed that the wild allotetraploid species A. *monticola* is a direct original species of the cultivated *Arachis hypogaea* L. (Seijo, Lavia et al. 2007). *Monticola* is similar to a donor wild diploid species thereof, and is also a completely procumbent species. In early genetic studies on *Arachis hypogaea* L. plant architecture, different materials lead to different results. Early studies on *Arachis hypogaea* L. plant architecture by Balaiah et al. show that the upright plant architecture is dominant to the procumbent plant architecture (Balaiah, Reddy et al. 1977). However, many late studies show that the procumbent plant architecture is dominant or incompletely dominant to the upright plant architecture. For example, Jiang Fu and Zhang Junwu found that, when procumbent and upright varieties were crossbred, an offspring $F_1$ was semi-procumbent (incompletely dominant), and an offspring $F_2$ involved three plant architectures: upright, semi-procumbent, and procumbent (Jiang Fu and Zhang Junwu 1982). Gan Xinmin, Cao Yuliang, et al. believed that the procumbent plant architecture was dominant relative to the upright plant architecture, and the segregation of $F_2$ generation conformed to the 3:1 (procumbent plant architecture: upright plant architecture) single-gene control mode (Gan Xinmin, Cao Yuliang, et al., 1984). Recently, a research group in Israel mapped a gene locus for controlling an *Arachis hypogaea* L. plant architecture from spreading to bunching within a 1.2 Mb interval on *Arachis hypogaea* L. chromosome B05 through grouping analysis, and predicted two most likely candidate genes, one of which is an FAR1 related gene essential for the far-red response controlled by plant pigment A, and the other one of which is a 1-aminocyclopropane-1-carboxylate (ACC) oxidase-like protein-related gene (Kayam, Brand et al. 2017).

Existing research is limited thereto. There is no systematic molecular genetic research on the *Arachis hypogaea* L. plant architecture represented by *Arachis hypogaea* L. lateral shoot angles/growth habits, and there is also no report about related genes for controlling the *Arachis hypogaea* L. lateral shoot angle or plant architecture and use thereof.

SUMMARY

In order to overcome the defects in the prior art, the present disclosure clones a functional gene LBA5 related to lateral shoot angles, growth habits, and a plant architecture of *Arachis hypogaea* L. from *Arachis hypogaea* L., and uses this gene and a homologous gene thereof to conduct biotechnological modification or genetic improvement on a plant architecture of *Arachis hypogaea* L. or another crop.

In order to achieve the above objective, the present disclosure adopts the following technical solutions:

The present disclosure provides use of a gene LBA5 for regulating lateral shoot angles, growth habits, and a plant architecture of *Arachis hypogaea* L. in crop genetic improvement, where the use preferably refers to use in the improvement of lateral shoot angles, growth habits, and a plant architecture of *Arachis hypogaea* L.

The gene LBA5 includes homologous genes LBA5b (from subgenome B) and LBA5a (from subgenome A) from two sets of subgenes of cultivated *Arachis hypogaea* L. and corresponding defunctionalized alleles lba5b and lba5a; functional LBA5b has a nucleotide sequence shown in SEQ ID NO: 1; at least three allelic variations have been found for defunctionalized lba5b at present, a common one among which is lba5b-1 with a nucleotide sequence shown in SEQ ID NO: 2; at least two other types of lba5b-2 and lba5b-3 have been found for the defunctionalized lba5b in germplasm resources, with nucleotide sequences shown in SEQ ID NO: 25 and SEQ ID NO: 26, respectively; functional LBA5a has a nucleotide sequence shown in SEQ ID NO: 3; and defunctionalized lba5a has a nucleotide sequence shown in SEQ ID NO: 4.

The present disclosure provides use of mRNA or cDNA encoded by genes LBA5b and LBA5a for regulating lateral shoot angles, growth habits, and a plant architecture of *Arachis hypogaea* L. in crop genetic improvement, where the use may preferably refer to use in the improvement of lateral shoot angles, growth habits, and a plant architecture of *Arachis hypogaea* L.; cDNA encoded by the gene LBA5b has at least four forms LBA5b.1 to LBA5b. 4, with nucleotide sequences shown in SEQ ID NOs: 5-8, respectively; and cDNA encoded by the gene LBA5a has at least two forms LBA5a.1 and LBA5a.2, with nucleotide sequences shown in SEQ ID NOs: 9-10, respectively.

The present disclosure also provides use of an amino acid, a polypeptide, or a protein encoded by genes LBA5b and LBA5a for regulating lateral shoot angles, growth habits, and a plant architecture of *Arachis hypogaea* L. in crop genetic improvement, where the use may preferably refer to use in the improvement of lateral shoot angles, growth habits, and a plant architecture of *Arachis hypogaea* L.; proteins encoded by the gene LBA5b have amino acid sequences shown in SEQ ID NOs: 11-12; and proteins encoded by the gene LBA5a have amino acid sequences shown in SEQ ID NOs: 13-14.

The present disclosure also provides use of promoters of genes LBA5b and LBA5a for regulating lateral shoot angles, growth habits, and a plant architecture of *Arachis hypogaea* L. in crop genetic improvement, where the use may preferably refer to use in the improvement of lateral shoot angles, growth habits, and a plant architecture of *Arachis hypogaea* L.; a promoter of the gene LBA5b has a nucleotide sequence shown in SEQ ID NO: 15; and a promoter of the gene LBA5a has a nucleotide sequence shown in SEQ ID NO: 16.

The present disclosure also provides a pair of primers for cloning an *Arachis hypogaea* L. gene LBA5b, including LBA5b-F and LBA5b-R with sequences shown in SEQ ID NOs: 17-18, where the primers can be used in cDNA of procumbent *Arachis hypogaea* L. to clone and amplify a complete coding frame of the gene LBA5b by PCR.

The present disclosure also provides a pair of primers for constructing an overexpression vector of a *Arachis hypogaea* L. gene LBA5b, including LBA5b-OE-F and LBA5b-OE-R with sequences shown in SEQ ID NOs: 19-20, where the primers are used in cDNA of procumbent *Arachis hypogaea* L. or a plasmid with the gene to amplify the gene LBA5b, and an amplification product is digested with an enzyme and ligated into an overexpression vector pHB to construct an overexpression transgenic vector.

The present disclosure also provides sequences for constructing a target for gene editing on a gene LBA5b, including sgRNA1 and sgRNA2 shown in SEQ ID NOs: 21-22, where the two fragments are ligated into an sgRNA region of a CRISPR/Cas9 vector to construct a gene editing vector for the target gene LBA5, and then the gene editing vector is transformed into *Arachis hypogaea* L. to realize the editing for the *Arachis hypogaea* L. gene LBA5.

The two homologous genes LBA5b and LBA5a of the gene LBA5 for regulating lateral shoot angles, growth habits, and a plant architecture of *Arachis hypogaea* L. according to the present disclosure may be directly derived from *Arachis hypogaea* L., and may also be derived from *Glycine max* L., *Brassica napus* L., *Gossypium* spp., *Oryza sativa* L., *Zea mays* L., *Triticum aestivum* L., or other crops.

Beneficial effects of the present disclosure:

In a first aspect, the present disclosure provides a gene LBA5 for regulating lateral shoot angles, growth habits, and a plant architecture of *Arachis hypogaea* L., including two subgenomic homologous genes LBA5b and LBA5a and corresponding defunctionalized alleles lba5b and lba5a. An expression level of the LBA5b can be changed to regulate an angle between an *Arachis hypogaea* L. lateral shoot and a main stem. The allelic variation lba5b is a non-functional allelic variation, and the non-functional allelic variation including two homologous genes of this gene can lead to an upright *Arachis hypogaea* L. plant architecture, thereby realizing reasonable close planting of *Arachis hypogaea* L. and increasing the yield per unit area.

In a second aspect, the present disclosure also provides a promoter sequence of the gene LBA5 for regulating lateral shoot angles, growth habits, and a plant architecture of *Arachis hypogaea* L., including promoter sequences of the two subgenomic homologous genes LBA5b and LBA5a. Editing or modification on the sequence can realize the control of an expression level of the LBA5 gene, thereby realizing the regulation of lateral shoot angles, growth habits, and a plant architecture of *Arachis hypogaea* L.

In a third aspect, the present disclosure provides a recombinant construct including a nucleotide sequence related to the LBA5 or allele lba5 described in the first and second aspects of the present disclosure, where the vector is an overexpression vector or an antisense RNAi vector.

In the present disclosure, the extreme individual analysis method based on genome sequencing and the extreme individual analysis method based on transcriptome sequencing are comprehensively utilized to map and clone the gene LBA5 for regulating lateral shoot angles, growth habits, and a plant architecture of *Arachis hypogaea* L. on *Arachis hypogaea* L. chromosome B05 (or called chromosome 15); on this basis, the orthologous gene LBA5a on the *Arachis hypogaea* L. homologous subgenome A is cloned by homologous cloning; the *Arachis hypogaea* L. variety population association analysis, molecular biology analysis, transgenic technology, and other methods are comprehensively utilized to prove the role of this gene and a promoter thereof in the regulation of lateral shoot angles, growth habits, and a plant architecture of *Arachis hypogaea* L., which provides a corresponding theoretical basis for high-yield breeding of *Arachis hypogaea* L. plant architecture improvement and also provides an important genetic resource for molecular breeding of *Arachis hypogaea* L. and plant architecture improvement of other crops; and through the function of the two homologous genes LBA5b and LBA5a of LBA5 in the regulation of lateral shoot angles, growth habits, and a plant architecture of a plant (especially a crop such as *Arachis hypogaea* L., *Glycine max* L., *Oryza sativa* L., *Zea mays* L., *Brassica napus* L., and *Gossypium* spp.), new functions and use of a crop such as yield capacity can be indirectly improved.

DETAILED DESCRIPTION OF THE EMBODIMENTS

The technology of the present disclosure is further illustrated through examples below. In the following examples, a method for mapping and cloning LBA5b and a homologous gene thereof, a method for verifying base differences among LBA5b alleles through sequencing, and use of a transgenic method to prove the function of the LBA5b gene are further described.

Figure 1:
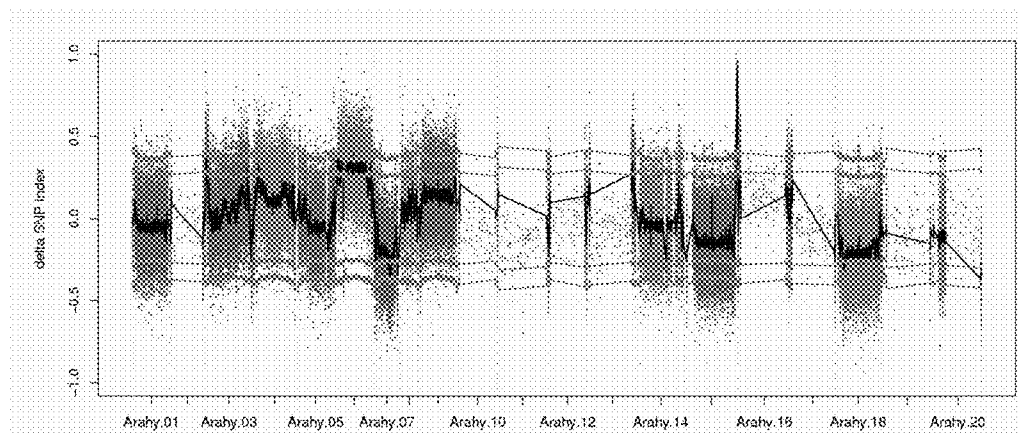
FIG. 1 shows the BSA-seq genetic mapping of the gene LBA5b using an HN-$F_6$ population according to the present disclosure.

Example 1: Preliminary Mapping of an *Arachis hypogaea* L. Lateral Shoot Angle Using the BSA-Seq Technology In this example, an *Arachis hypogaea* L. variety Xiaohongmao of a procumbent plant architecture that had a basal angle of 900 between a lateral shoot and a main stem and an *Arachis hypogaea* L. variety Henan Nanyang of an upright plant architecture were used to construct a hybrid combination, and a line breeding method was used to obtain a recombinant inbred line RIL-HN-$F_6$ composed of 223 individuals; the lateral shoot angles, growth habits, and a plant architecture were investigated for the recombinant inbred line, and 30 of the individuals that had large lateral shoot angles and were more similar to the Xiaohongmao parent were selected and 26 of the individuals that had small lateral shoot angles and were more similar to the Henan Nanyang parent to constitute 2 DNA mixed pools P (procumbent) and Z (upright); sequencing was conducted on a machine, with a parental sequencing depth of >20×and a mixed pool sequencing depth of >30×, and a sequencing result was compared with a genome of the published cultivated *Arachis hypogaea* L. variety Tifrunner (a reference); with the upright plant architecture as a mutant plant architecture, SNP-index was calculated based on two progeny mixed pools, and a distribution map of the SNP-index of the two progeny mixed pools on each chromosome was plotted through a 2M sliding window; theoretically, a peak with an SNP-index value deviating from 0.5 was considered to be a result of trait selection, but due to the existence of distorted segregation, the presence of false QTL peaks could not be determined; and thus SNP-index of a wild plant architecture (a procumbent plant architecture) was subtracted from SNP-index of a mutant plant architecture (upright plant architecture) to obtain ΔSNP-index (FIG. 1). In order to eliminate the interference of distorted segregation, the same sliding window was used to plot a ΔSNP-index trajectory map, which could accurately screen out a target interval. Calculated ΔSNP-index was subjected to 1,000 permutation tests, the 95% confidence interval and 99% confidence interval levels were used as thresholds for screening, and results were given.

It can be seen from FIG. 1 that SNPs beyond the 99% confidence level only existed on the three chromosomes of chromosomes 3, 6, and 15, where the chromosome 15 exceeded a threshold line very obviously and the highest ΔSNP-index was as high as 1.0; it could be preliminarily inferred that there was a major locus related to the lateral shoot angle at an end of the chromosome 15; and most SNP loci beyond the 99% confidence level appeared on the chromosome 15, the ΔSNP-index≥0.5 accounted for 74.6% of all SNP loci beyond the 99% confidence level, and thus it could be inferred that there were a major locus at 153.8 M to 159.6 M on the chromosome 15.

According to a BSA-seq mapping result, 31 pairs of InDel markers between the two parents Xiaohongmao and Henan Nanyang on the chromosome 15 of *Arachis hypogaea* L. were developed and analyzed to obtain 19 pairs of InDel markers with prominent codominance and gel analysis effects between the two parents Xiaohongmao and Henan Nanyang, and the 19 pairs of InDel markers with prominent parental codominance were used to conduct genotyping for 192 members selected in the HN-$F_6$ population; according to genotypes of InDel markers, a genetic map construction module in the software QTL IciMapping was used to conduct local genetic map construction, with LOD=3.0 as a threshold, a linkage group coverage genetic distance of 192.19 cM, and an average distance of 17.47 cM among markers; a value was assigned for a phenotype of the HN-$F_6$ population: procumbent plant architecture: 90°, semi-procumbent plant architecture: 50°, and upright plant architecture: 10°; then in combination with a plant architecture of a population marker and the above genetic map, a mapping module in the software QTL IciMapping was used to conduct QTL mapping, and the inclusive composite interval mapping for additive and dominance (ICIM-ADD) was used to conduct iterative sampling 1,000 times to determine an LOD threshold, where the LOD threshold was 2.50, a major locus on the chromosome 15 was mapped between markers J15-11 and J15-12 with a contribution rate of 44.59%, and an enhanced locus was from Xiaohongmao, which could theoretically increase the lateral shoot angle by 25.91° C.; and InDel markers discovered by re-sequencing and the entire population of HN-$F_6$ were used for linkage mapping to verify the BSA-seq mapping result and define the locus between 156859290 bp to 157561753 bp on the chromosome B05 (an interval of about 702.46 kb).

Figure 2:
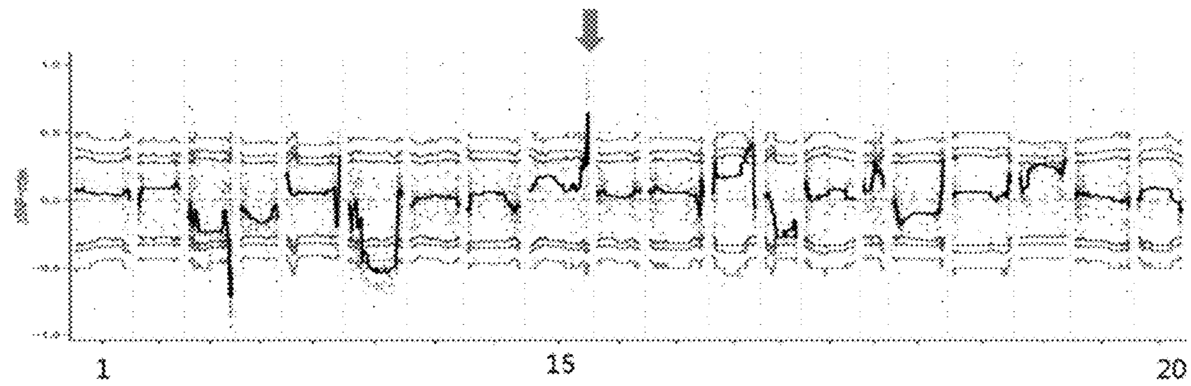
FIG. 2 shows the BSR-seq genetic mapping of the gene LBA5b using a PF-$F_5$ population according to the present disclosure.
Figure 3:
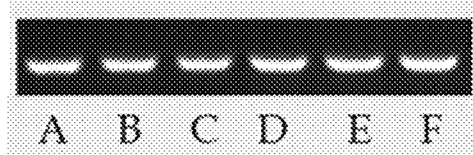
FIG. 3 shows the expression level analysis of the genes LBA5a and LBA5b in stem ends of lateral shoots of three upright varieties and three procumbent varieties according to the present disclosure.

Example 2: Mapping of an *Arachis hypogaea* L. Lateral Shoot Angle Using the BSR-Seq Technology In this example, another upright variety Pingdu 9616 and a procumbent variety Florunner were used to construct a recombinant inbred line PF-$F_5$, and 30 procumbent members and 30 upright members were separately selected from the recombinant inbred line; transcriptome sequencing was conducted for the two parents, the 30 procumbent members, and the 30 upright members, where a sequencing output for each offspring generation was no less than 3Gb Clean Date, and a sequencing output for each parental sample was no less than 6Gb Clean Date; a sequencing result was compared with a genome of the published cultivated *Arachis hypogaea* L. variety Tifrunner (as a reference); and with 30 individuals as a mixed pool, SNP data obtained from the transcriptome sequencing were used to calculate ΔSNP-index for a procumbent pool and an upright pool (FIG. 2), and the loci related to the lateral shoot angles, growth habits, and a plant architecture of *Arachis hypogaea* L. were also mapped at an end of the chromosome B05, which coincided with a mapping result of the HN population. According to an SNP genotype of each individual, an interval range was defined between 153809051 bp to 158407822 bp on the chromosome B05. A gene expression level was analyzed for the 30 procumbent individuals and the 30 upright individuals, results showed that there was a differentially expressed gene (DEG) in a mapping interval, which strictly conformed to the rule that the gene was highly expressed in both the procumbent parents and individuals, but was almost not expressed in the upright parents and offsprings. The gene was initially determined as a candidate gene for LBA5b, and the gene from the chromosome B5 was named LBA5b (SEQ ID NO: 1), which had at least four different transcription modes (SEQ ID NOs: 5-8). A homologous gene derived from the chromosome A05 was named LBA5a (SEQ ID NO: 3), which had at least two transcription modes (SEQ ID NOs: 9-10). Then the expression levels of LBA5b in Tifrunner, Florunner, *Monticola*, Xiaohongmao, Pingdu 9616, and Henan Nanyang were analyzed (see FIG. 3), and it could be known that the LBA5b was not expressed or expressed at a low level in upright cultivated *Arachis hypogaea* L., and the LBA5b was expressed at a high level in procumbent cultivated *Arachis hypogaea* L. As a result, it can be concluded that the LBA5b gene is one of the key gene loci for controlling lateral shoot angles of *Arachis hypogaea* L.

Example 3: Gene cloning and structure and function prediction for LBA5b (1) Gene Cloning for LBA5b:

Total RNA was extracted from a stem end of a lateral shoot of the procumbent *Arachis hypogaea* L. Tifrunner, and reverse-transcribed into cDNA. A cloning primer pair B5cd-F/R (with sequences of SEQ ID NO: 17/18) was used to conduct PCR amplification with the Tifrunner cDNA as a template. A PCR product was recovered and purified through gel, then ligated into a T vector, and transformed into *Escherichia coli* (*E. coli*), sequencing was conducted, and a strain with a correct sequence was reserved for later use. Specifically, in the PCR amplification, a PCR system (25 μl in total) included: 2×Gflex PCR Buffer ($Mg^{2+}$, dNTP plus): 12.5 μl, Template: 1 μl, 10 μm upstream and downstream primers: 1 μl for each, Tks Gflex DNA Polymerase: 1 μl, and water: the balance; and a PCR procedure included: pre-denaturation at 94° C. for 1 min; denaturation at 98° C. for 10 s, annealing at 55° C. for 15 s, and extension at 68° C. for 30 s, with 35 cycles.

(2) Gene Structure Analysis for LBA5b:

It was found that a cloned LBA5b gene had 4 transcription modes, with two in the 5'UTR region and two in the coding region. In a first mode, 212 amino acids were encoded, and in a second mode, 227 amino acids were encoded. The first mode was dominant in transcription. Through domain analysis, it was found that an LBA5b protein was an MADS transcription factor with two protein domains of MADS and K-box for the MIKC plant architecture.

Genome sequencing and methylation analysis of this gene in multiple procumbent and upright varieties showed that a promoter of this gene (SEQ ID NO: 15) had no significant difference in sequence and methylation level among the varieties. However, in the upright variety Shitouqi or Fu peanut, there was a double-base TA insertion in the first exon coding frame of the gene, such that a reading frame of the gene eventually underwent frameshift, a protein with a full function could not be formed, and thus the gene failed to be expressed; and the allelic variation was named lba5b-1 (SEQ ID NO: 2). Sequencing, enzyme digestion, or other means was used to determine whether there is the TA insertion mutation in *Arachis hypogaea* L. germplasm resources, and it was found that the TA insertion/deletion mutation was closely related to the upright/procumbent plant architecture of *Arachis hypogaea* L. In the upright varieties Luhua 11, Huayu 36, and Shanhua 11, there was a deletion of 1,870 bp in the first intron of the gene, and the gene was not transcribed, resulting in the upright plant architecture; and this allelic variation was named lba5b-2 (SEQ ID NO: 25).

In the upright variety MJX7, there was a deletion of 985 bp that started from the 5'UTR region and included a first exon, and this gene was severely incomplete, resulting in the upright plant architecture; and this allelic variation was named lba5b-3 (SEQ ID NO: 26).

Figure 4:
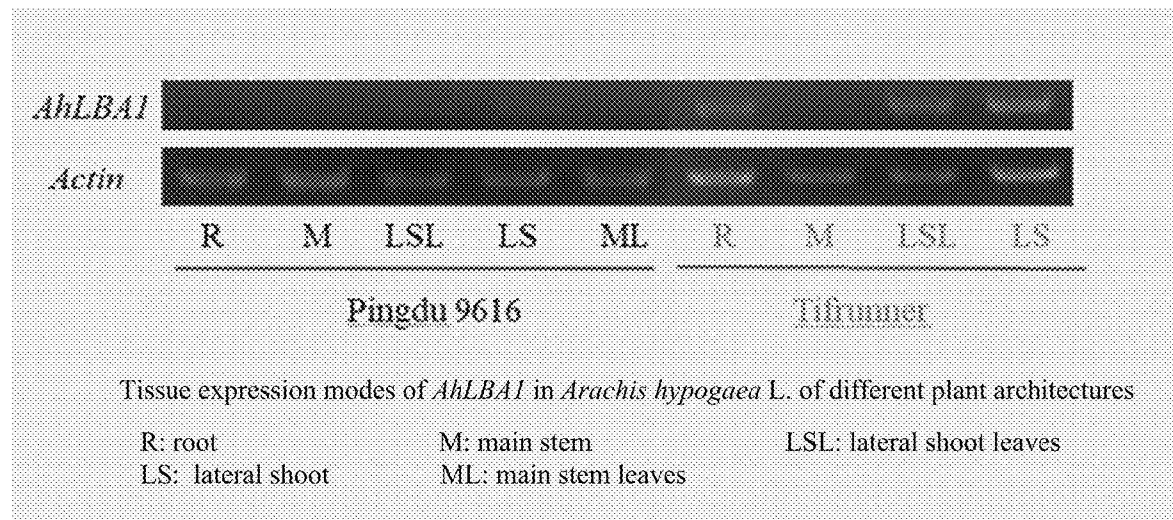
FIG. 4 shows the expression analysis of the gene LBA5b in different tissues of procumbent varieties and upright varieties according to the present disclosure.
Figure 7:
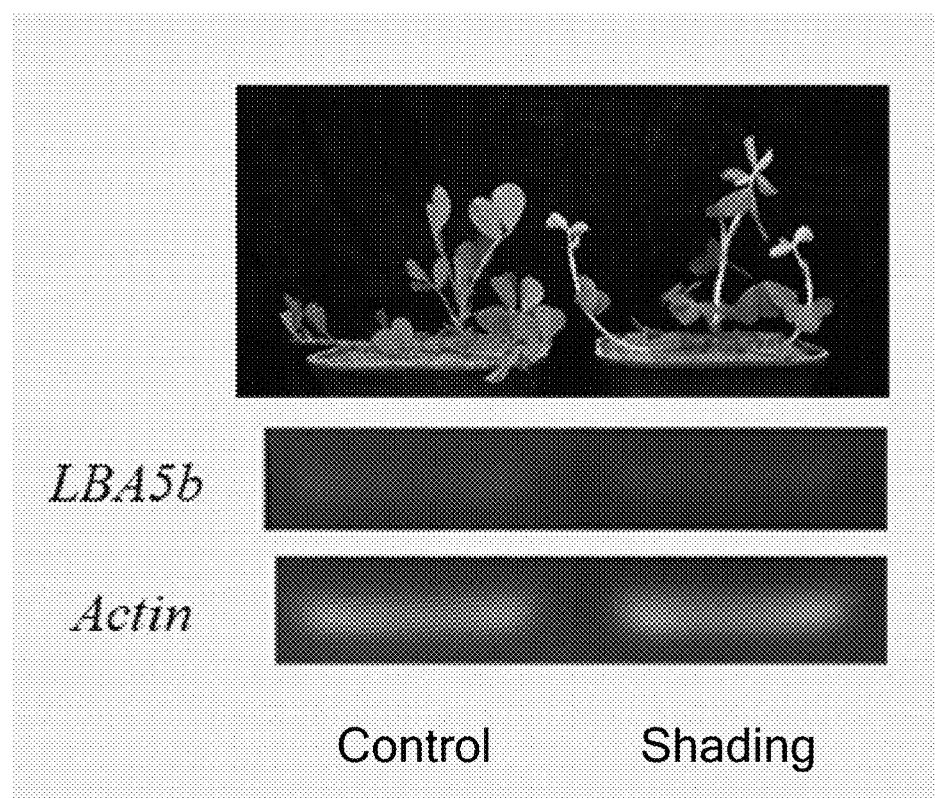
FIG. 7 shows the reduction of a lateral shoot angle of procumbent *Arachis hypogaea* L. varieties after shading and the change of an expression level of the gene LBA5b after shading according to the present disclosure.

(3) Genetic Characteristics Analysis for LBA5b:

According to gene annotation, the *Arachis hypogaea* L. LBA5 encodes an MADS transcription factor for the MIKC plant architecture (MIKC_MADS gene family). The most homologous gene in *A. thaliana* is AT2G45660 (AGAMOUS-like 42), and thus this gene is also called AhAGL42 (AGAMOUS-like 42 of *Arachis hypogaea* L., referred to as LBA5 in this example), which is also a member of the MIKC_MADS gene family. AT2G45660 (AGAMOUS-like 42) plays an important role in the development and regulation of *A. thaliana* at a flowering phase, but plays no role in the regulation of a lateral shoot angle, and in this example, it was found for the first time that the gene has the function to regulate lateral shoot angles, growth habits, and a plant architecture of *Arachis hypogaea* L. Tissue transcriptome sequencing analysis and real-time fluorescence quantitative tissue expression profile analysis for the gene LBA5b showed that, in the procumbent varieties, LBA5b was predominantly expressed in the leaves, needle tips, and pistils of lateral shoots, but expressed at an extremely-low level in the main stem leaves (see FIG. 4). Shading can significantly reduce an expression level of the gene LBA5b, and can also significantly reduce an angle between a lateral shoot and a main stem (see FIG. 7). It is inferred that RNAi, antisense RNA, and other technologies can be used to regulate an expression level of this gene, thereby accurately regulating an angle between a lateral shoot and a main stem of *Arachis hypogaea* L.

Cloning and sequencing for the LBA5a gene in the procumbent and upright varieties of cultivated *Arachis hypogaea* L. showed that a coding region of this gene had no difference among the varieties. However, compared with a donor AA genome of the wild variety *Arachis* duranensis (A. duranensis), a coding frame of the gene had a C base deletion, resulting in the premature termination of an encoding protein; and the allelic variation was named lba5a (SEQ ID NO: 4). Through expression analysis by ordinary RT-PCR, it was found that, in both the upright variety and the procumbent variety, LBA5a was not expressed in the main stem (or expressed at a very low level), and expressed at a high level in lateral shoots; but the expression level in the procumbent variety was significantly higher than that in the upright variety. It was also found that, in the procumbent variety, the expression level of LBA5a was about ¼ lower than the expression level of LBA5b (see FIG. 2). The promoter sequences of LBA5b and LBA5a were analyzed, and many differences were discovered. It could be inferred that the expression difference was caused by the differences in the promoter sequences of these two genes. Based on this, it was proposed that the promoter sequences of these two genes could be changed to change the expression levels of the two genes, thereby regulating lateral shoot angles, growth habits, and a plant architecture of *Arachis hypogaea* L.

Through continuous backcrossing, the TA insertion mutant allelic variation lba5b of LBA5b was introduced into the procumbent variety Tifrunner, and it was found that an angle between a lateral shoot and a main stem of Tifrunner$^{lab5b}$ was significantly reduced, and thus more individual plants could be planted in the same land, thereby increasing a yield per unit area of *Arachis hypogaea* L.

Example 4: LBA5b Overexpression Transgenesis can Increase an Angle Between a Lateral Shoot and a Main Stem of *Arachis hypogaea* L In this example, 35S was used as a promoter to construct an overexpression vector, and the overexpression of LBA5b was achieved in an upright variety by the pollen tube introduction method. Specific steps were as follows: a T plasmid with the LBA5b gene and an overexpression vector plasmid pHB were separately digested with HindIII and pst1; a target fragment and a pHB plasmid vector backbone fragment obtained from enzyme digestion were recovered and purified through gel, and then ligated overnight by a T4 ligase; a ligation product was transformed into competent *E. coli* DH5a by heat shock, and then the competent *E. coli* was coated on a LB plate with kanamycin; single colonies were picked for PCR detection, positive colonies were sent to a biological company for sequencing, and correct strains were selected for shaking cultivation; a plasmid with the target fragment was extracted, which was an LBA5b overexpression plasmid: pHB-LBA5b; the LBA5b overexpression plasmid was transformed into competent *Agrobacterium tumefaciens* (*A. tumefaciens*), then the *A. tumefaciens* was coated on a YEB plate with kanamycin and rifampicin, and single colonies were picked for PCR detection to obtain positive colonies for later use, which were transgenic strain; and the overexpression vector with the LBA5b gene was transformed into the upright cultivated *Arachis hypogaea* L. Huayu 23, and positive individuals were screened out to observe the change in the lateral shoot angle.

Figure 5:
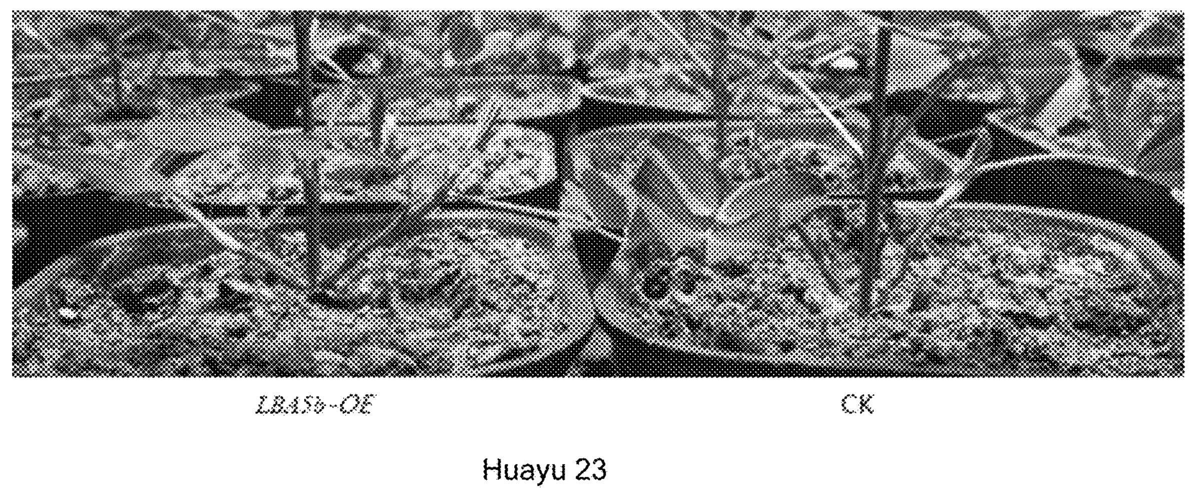
FIG. 5 shows the phenotypes of upright varieties with transgenic overexpression of the gene LBA5b according to the present disclosure.

The positive plants can be screened out by introducing a gene into a vector, and can also be determined by detecting an expression level of LBA5b. Phenotypic analysis of positive plants showed that the overexpression of the LBA5b gene in Huayu 23 can increase an angle between a lateral shoot and a main stem (see FIG. 5), proving that the LBA5b gene has the function of increasing a lateral shoot angle of *Arachis hypogaea* L.

Example 5: Knockout of LBA5b Through Gene Editing can Reduce an Angle Between a Lateral Shoot and a Main Stem of *Arachis hypogaea* L.

In this example, the CRISPR/CAS9 system was used to conduct knockout through gene editing. Specific construction steps were as follows: a gRNA target sequence was designed and generated online (http://www.biogle.cn/index/excrispr), and two targets sites sgRNA1 and sgRNA2 (SEQ ID NOs: 21-22) with the highest score were selected; a generated Oligo sequence was synthesized by a biological company, and synthesized Oligo was dissolved in water to 10 μM, and 18 μl of Buffer Anneal, 1 μl of Up Oligo, and 1 μl of Low Oligo were mixed in a 200 μl PCR tube, heated at 95° C. for 3 min, and then slowly cooled to 20° C. at a rate of about 0.2° C./s to prepare a Oligo dimer; the Oligo dimer was introduced into a CRISPR/Cas9 vector; 2 μl of CRISPR/Cas9 Vector, 1 μl of the Oligo dimer, 1 μl of Enzyme Mix, and 16 μl of $ddH_2O$ were thoroughly mixed in a 200 μl PCR tube to allow a reaction at room temperature (20° C.) for 1 h; a ligation product was transformed into competent *E. coli* DH5a by heat shock, and then the competent *E. coli* was coated on a LB plate with kanamycin; single colonies were picked for PCR detection, positive colonies were sent to a biological company for sequencing, and correct strains were selected for shaking cultivation; a plasmid with the target fragment was extracted, which was an AhLBA knockout plasmid: BGK041-AhLBA-½; the AhLBAb gene knockout plasmid BGK041-AhLBA-½ was transformed into competent *A. tumefaciens*, then the *A. tumefaciens* was coated on a YEB plate with kanamycin and rifampicin, and single colonies were picked and subjected to PCR detection with the primer pair CS4-F/R (SEQ ID NOs: 23-24); positive colonies were selected and transformed into *Arachis hypogaea* L. BGK041 was used as the CRISPR/Cas9 vector. The vector used the *Glycine max* L. U6 promoter to drive the SG sequence, which can be efficiently used for dicotyledonous plants. An enhanced CaMV promoter was used to achieve the efficient expression of the Cas9 protein.

Figure 6:
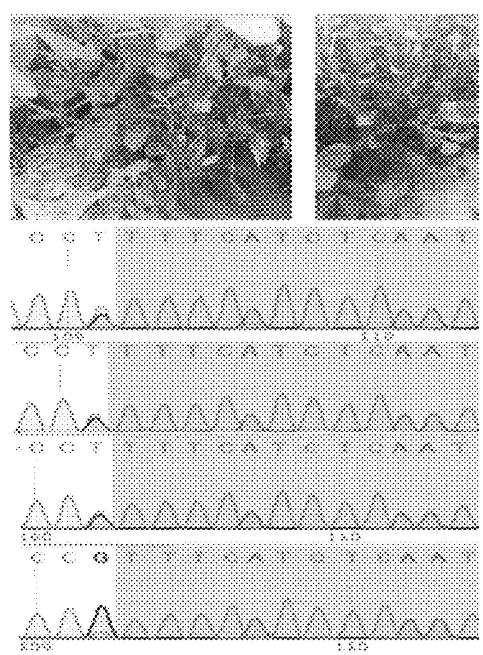
FIG. 6 shows the effect of gene editing on the gene LBA5b in procumbent varieties according to the present disclosure.

Transgenic plants were subjected to PCR detection with the primer pair of CS4-F/R to determine whether the vector sequence was introduced. Genetic sequencing of the target gene LBA5b was conducted for positive transgenic plants, and offsprings whose target sequence LBA5b changed were detected (see FIG. 6). Individuals undergoing gene frameshift mutation or premature termination were selected, and it was found that a lateral shoot angle changed from procumbent to upright. That is, the knockout of the gene can significantly reduce an angle between a lateral shoot and a main stem of an offspring.

Example 6: Nucleic Acid and Protein Sequences

TABLE 1

Sequence names and origins of SEQ ID Nos: 1-26

| SEQ ID NO. | Name | Origin |
|---|---|---|
| 1 | LBA5b gDNA sequence | *Arachis hypogaea L.* variety Tifrunner |
| 2 | lba5b-1 gDNA sequence | *Arachis hypogaea L.* variety Shitouqi |
| 3 | LBA5a gDNA sequence | Wild diploid *A. duranensis* |
| 4 | lba5a gDNA sequence | *Arachis hypogaea L.* variety Tifrunner |
| 5 | LBA5b.1 cDNA sequence | *Arachis hypogaea L.* variety Tifrunner |
| 6 | LBA5b.2 cDNA sequence | *Arachis hypogaea L.* variety Tifrunner |
| 7 | LBA5b.3 cDNA sequence | *Arachis hypogaea L.* variety Tifrunner |
| 8 | LBA5b.4 cDNA sequence | *Arachis hypogaea L.* variety Tifrunner |
| 9 | LBA5a.1 cDNA sequence | Wild diploid *A. duranensis* |
| 10 | LBA5a.2 cDNA sequence | Wild diploid *A. duranensis* |
| 11 | LBA5b.1 protein sequence | *Arachis hypogaea L.* variety Tifrunner |
| 12 | LBA5b.2 protein sequence | *Arachis hypogaea L.* variety Tifrunner |
| 13 | LBA5a.1 protein sequence | Wild diploid *A. duranensis* |
| 14 | LBA5a.2 protein sequence | Wild diploid *A. duranensis* |
| 15 | LBA5b Promoter gDNA sequence | *Arachis hypogaea L.* variety Tifrunner |
| 16 | LBA5a Promoter gDNA sequence | *Arachis hypogaea L.* variety Tifrunner |
| 17 | LBA5b-F cloning primer sequence | Artificial sequence |
| 18 | LBA5b-R cloning primer sequence | Artificial sequence |
| 19 | LBA5b-OE-F overexpression vector primer | Artificial sequence |
| 20 | LBA5b-OE-R overexpression vector primer | Artificial sequence |
| 21 | sgRNA1 target sequence | Artificial sequence |
| 22 | sgRNA2 target sequence | Artificial sequence |
| 23 | CS4-F Cas9 detection primer | Artificial sequence |
| 24 | CS4-R Cas9 detection primer | Artificial sequence |
| 25 | lba5b-2 gDNA sequence | *Arachis hypogaea L.* variety Luhua 11 |
| 26 | lba5b-3 gDNA sequence | *Arachis hypogaea L.* variety MJX7 |

What is claimed is:

1. A method for regulating a lateral shoot angle, a growth habit, and a plant architecture of *Arachis hypogaea* L. for crop genetic improvement comprising gene editing of a gene LBA5b to improve the lateral shoot angle, the growth habit, and the plant architecture of the *Arachis hypogaea* L.; wherein the gene LBA5b of an *Arachis hypogaea* L. plant is edited resulting in a defunctionalized lba5b allele that reduces a shoot angle between a lateral shoot and a main stem of the *Arachis hypogaea* L. plant compared to a procumbent *Arachis hypogaea* L. plant having 90° shoot angles between lateral shoots and a main stem.

2. The method of claim 1, wherein editing the gene LBA5b regulates the lateral shoot angle leading to an upright *Arachis hypogaea* L. plant architecture.

3. The method of claim 1, wherein editing the gene LBA5b comprises expressing varying levels of the gene LBA5b resulting in an upright *Arachis hypogaea* L. plant architecture.

4. The method of claim 1, further comprising editing the LBA5a gene from the *Arachis hypogaea* L. plant to result in a defunctionalized Iba5a allele.

5. The method of claim 1, wherein the gene LBA5b is represented by SEQ ID NO: 1.

* * * * *

SEQUENCE LISTING

```
<160> NUMBER OF SEQ ID NOS: 26

<210> SEQ ID NO 1
<211> LENGTH: 8859
<212> TYPE: DNA
<213> ORGANISM: Arachis hypogaea L. variety Tifrunner
<220> FEATURE:
<221> NAME/KEY: misc_feature
<222> LOCATION: (1)..(8859)
<223> OTHER INFORMATION: Genomic nucleotide sequence of LBA5b from
      Tifrunner

<400> SEQUENCE: 1

aagaagaaga tggtgagagg aaagattgag atgaaaagga tagagaatgc aacaagccgt     60

caagtaacgt tttcaaagag gaggagtggg cttctaaaga aagcacatga gctttctgtt    120

ctttgtgatg cacaaattgc tcttataatc ttttcacaaa gtgggaggct ctttgaatac    180

tcaagtactt cagagtaagc ccttacttaa tcactttatt ttcttgcttc atcaacattc    240

atgttagtgt tagtttcatt ctttaatttt tattcttctc ctaattaatt agtacaatac    300

tactacttat tattgaacta ttatatatat ggtttaatct tggagaaact aaaggtttac    360

tttaatttgc tcaaactatg atacatgtgt tttgttgtga gttgtgctaa gtcttcctca    420
```

-continued

```
aactacctag atttgatgat caaagaacat ggatctcatt gaaaaaaaag tgtgtggctt    480
tccgtttatg gtaagctaac tactactggt aattacaaaa gtatatacac taatttagaa    540
atactcaaca cttgctaaat tgtagtagta gcatttggtt gctgaataaa ttggaacttg    600
aaatactctg ctatgtaatt atttcaatgc tctccgtatc aaataaggta aaaaaaaaat    660
ggtttttaa aatttttct aagatattat atagtgtatt tttcattata catgttttaa    720
gtgagattaa gaaaaaaata tgtgaagagc aaagatatat tgtagtatta caaaagacca    780
tcacctttg caacattact taagaaaaaa aaaaacctaa gattacctat ttttatttga    840
tgttgagttt agttctgcaa tctgctctgt actaattata tctttatcct aaatataaca    900
aagaggagtg ctaaggggcc agcagatttt gtgagttgta gccatcaatt agtcatcaat    960
agtgtattta atggtgtgag atttcatcta acggtggaga atcactcatt tttttttgc   1020
tggctaagta ttggccagat tttaataaat ctgctggccc ctagactttt cctataacga   1080
atgctgcatt ctttttctt ttttttttct tttctcccct ataatttgct agattatcat   1140
tgatccttat tatgaaatta tttatttcaa agagacacat gcaagagtct cttgagtttt   1200
taagttgaaa agtgaattat ggataggtct tttttgtttt atattaaaat tctattttt   1260
gtttaaaaaa atgagagtaa caattttata aaaaaagtaa aaactaacat ggactaaaag   1320
tctgattgat ttgtatttgt aatttttta tttttaatac tttgtgaaaa aatattaaat   1380
aaaaaactgt aaaattatat attttatttt attttatttt ttacaaaatt ctttaaaaaa   1440
tatgaaaata gaattgcaat gaacttgtaa actaatctct tttgtccttt gttctgatct   1500
cttattactt cttgaatata aaaaaaaaaa cactaactaa agtagtaatt cacagaacta   1560
tagtacaatt atctgcattt tttatgataa tagttcagga aattgcattc tcatcacgtc   1620
tttcgaatac taattgagac atacatggtg ggagttttgg cagaacaaga aagggggaa   1680
catgttcagg tgctgccatg tgttcatgcg gtttattttt cccatgacca actttgctca   1740
ttctaaattc ctttctttaa acactttttt tttttaatat aatttagaaa aaactttcaa   1800
gtatacccgt atattagtgt tttagtcatt tttaacggtt gatcttaatt atatattata   1860
tatatttttt gtaattaaga tcaacggtta aaaattatta aaacaccatt atacttgtac   1920
actttaaagt ttttctataa cttattttat ggcaataaca catctatgta tatatatgtc   1980
ttttcctaac ctaggaactg ggaagatatt gtagctatct ttttttttt ttttaactct   2040
taatagtgtg ttttgatttt ggctctgcta gttagtagca atgaagaagt tctatgaagc   2100
tataatatct tcaaaaaaga ttatacaata gaaatagaat agtgggtgta gataggccta   2160
caatgggtat gtagcagcaa gatttccaaa tctagggttt tgacatatac atttcctatc   2220
tcaatagatc ttcaattaag aggctatata atctaaatgt tgcaatgtag ggtttgtagc   2280
cttgaagcac atgcatattt catttatttg cttctctttt attgtattat gttttctttt   2340
gttaattgaa tgaaggaatt tttgttagat agtatatatg tacttaaatg caaggctaaa   2400
tattcatatt tactttagat gaatataaaa ttaaatctga tgaatttctc cttgtttttg   2460
tctgaaattc aactcatgta tagtcagact attttctgta tgataggtga acatatatat   2520
atttttaaaa aataatatta tgtacataca aaaattaatc accaaattag ttatcatgta   2580
gttagatata tttaaacatg ttacatacat tttcaatgtg tatttatgag tagttgattt   2640
gactattgat ttttagtgtg catttagtgc agttattttt cctcagtgaa ttgattttca   2700
tttttttgta atttaaatgt tatatttaag catttaatat taatttttga aaataaaaaa   2760
tgaacccata agatgtgata aatcgcaaat cttgaatgca aaaggctagt ttttttttt   2820
```

```
ttttaagccc taattatcat agcaagtaaa caggttaatc caataggttt atgtcattta   2880
gtgcatggtg ggtcaataga tccctgtttt ttcaactcat gatgtaataa tactccttat   2940
tttcacattt tatgctccaa cttttgtatc tcataacatt catgtagaaa atatggatta   3000
acctgaactt ggagattttt ttaaaaaaaa aatcatatta attaactgta tatcttcatc   3060
ataggaatgc ctgcaaagtt ttttgctgac attaatgaat aatataatgt tctgattgct   3120
ttgttttcaa tagctacctc ttaacagtat atgtttttaa tttctttgaa atgtttcagc   3180
atggaacaaa tgttggaacg ctaccgtcaa tatgtagcag atgatggtcg tatcaataat   3240
attggagaat tccaggtata gtaaagagaa tatctataat ggtatagtta agttaccatt   3300
taccgctacg ataccaacag tatttctgtc aacttctgct aacttttatt tataactgtg   3360
tttaatggaa gtgtttttct ggatgtgtct aataaaaatg tctttttat gactgagtct    3420
aataaaagtg tttttataaa tgtatttttt ggatgtgtct ttttatacat gtgcttaaaa   3480
tataataatt aattattgtt ggcaataaat tgacagataa cctattggta ccctatattt   3540
ttcctttacc aatatatata atatatattg actataatac cttttagttc ttttaaaatt   3600
tcaggattat ttaataatat atagttttat ttatttgtag tatgaaaacc tatatatatt   3660
tcatcaagac aactatttgg agctagcagc tagctactcc taataagtaa taagcatgcg   3720
atattgatat tcatagcaca tttaatttga taagaaagtg aagattatta ataacacacg   3780
accagatcaa tatataatat tcatgtcatg ccatgctatt aatttttttgg gattattaaa  3840
gatataacta tttatgtaat tttttcgtca atttaagttt ttagaaaaag tagtttcatt   3900
agatggtata agagtttatt ggcatctaga gtaaataaat ttattaatgt ggctgtttta   3960
ttattatact tcctccttct taaattatct gattcttttt tattttttta tttttgttac   4020
atttttagtt ttaagaagtt attaattaat ttgtttcact ataaattaaa aaagttagaa   4080
gaatagaatt atgaatggaa agagaaatta atattaagaa catttttctt ttttttttgtt  4140
tgttctttac attttttat aaaatttaat gattatttta gtaattatat aattaaaaag    4200
agacagatag gtaagagtaa cgttttatat atagtaaaaa ttaaattata atggattgta   4260
ataaaattgg ttttatgctt tgacatgcag caattggaat ttgatccccc aagcttggct   4320
aagaagattg aacttcttga gctttctcaa aggtcaatcc tgtgtttaaa tactaatccg   4380
tttattgctg ttgttcatat tctaatactg agtattatat tcattaatat ttggtgtgcc   4440
atgaaatttt aattcattgt ttgaatttgt taggaagcta atgggacagg gcctgagctc   4500
ttgttcattt gatgaactcg ttggaattga gaatcagctt gtgtcaagct tgcaaaacat   4560
taggctcaaa aaggtcatta ataattcaca acattatatt atattatata gatgtatata   4620
tatataagaa caagacgttc ttaatttaat taatttaatg tactttcagg ctcagcttta   4680
tagagagcat attgaacaac tacaaaataa ggtacctgag cttagtttgg atgcaaatta   4740
tacatcttta aagaattaaa aaaaattgta taaattattt taattaggtt tcatggtgga   4800
catctgacac atttttatgt attgaatcca ggagaaggat ttgctcctag agaatgccaa   4860
attaactgaa atggtgagtt accattttct tttcatgatt tatagctggt ttgacaaatt   4920
tatttagaaa gttatttata attttattgt gtttggtaaa taaaaaaata atgcgattgt   4980
atttgtagtt ttaaaaagtt tgaagtattt tgaaacaaaa atattatgtt tacactaaaa   5040
attcgttatt aaataagttt ttatgtattt gtatataaat aaatatgtag tttaatttat   5100
ttttaatgag tttagtagct tatttttgta gatatttagt atggttgatt ttgaaagcac   5160
```

-continued

```
ttaagaaaat atttttaaa gttagtttgt gtttattaaa attaaaatgt ataatatata   5220
tttatatatt aataaatatt taaatttatt cttatattaa aaagtataat ttttgtctct   5280
aaaattttca aaatatctgt aacgtaaaat ttgtttcaat tttgtttcta acattttaaa   5340
tatatttcaa ttataccttt gagggtaggg gtggcaatcg aggaagtccg ctccgtcaaa   5400
agcccgccat ctggtgggtc tactaaatct cttttttttt tttttatgaa ctattaaata   5460
ttaaataata tatataattt cataactatt ttaataaatt tataatttct aaatctacaa   5520
acaataaagt cttcataatt ataaatatat aataaacata attataaata aaattttttg   5580
aaacaaaata taaacattgt tcaaaatata taattaaaca tcttcaaatt tataatcaat   5640
caaatataaa acataatcca aaatataatt tagaacatct ttaattatct acaacctctt   5700
gtgtttgtaa aaaaatgtcc ttgaccaaaa agacgcctgg ttcggtgggg aagcccgctc   5760
cgtcctgtca aaatccacgg attaagcgat gcgggttaga cagattttta ggtttgacgg   5820
ttttaaattt tcagtcgttc aacccgtctt ttttagtggg ttatacggac taatctgatg   5880
aattttggcc cgtttgtcac ctctttttga gggttaacac tattaatgga gatgctattg   5940
tgacaattat gtgctgacat gtcactaaaa cgtggtaaaa ctcagctatt aacatgtcag   6000
ggtagtactg tcatgttatt tgttatccaa ctaaggaata taattgaaat ataaaaaacc   6060
aagttgagtt ggtctagtgg tgagctcatt ggtttgctta aacaagtgtt ttaaatcccg   6120
ccttgtgcat gcagcaacct attggccagt gacaaaccct taaatggagc ttagtactga   6180
ggcggattag tccttggcct accgggttgg aggataccgt ggccaaggat accgtggaaa   6240
aaaaaaagaa atataaaaag taaaattaaa actaaatgtt aaaagataaa atgtgaacat   6300
tgaggataaa aatagaattt attactctat tatttttaaa taaaaaaatat attaataata   6360
ttcttaaaat atatcaggtt tattgagatt tattttaata caataatatt tttactaaaa   6420
aattatgata agaactacat attcttctta caaaattata aaaaatattt taaaaatgta   6480
tcatttttaa tacataaaaa tagctttgat acctttaaaa atttctttag taatactttt   6540
aataatttgc taacaaacat gtgattatga caactaatta agtattatat agacttatta   6600
gtaaattata taaaaatatt ttaaaaagta tccaagtgat ttttatataa taaaagttat   6660
atttttaaa atatttttat ataattttct aaaattttat agtatttata aaaagattta   6720
ttttcaataa aagatattat tatattaaaa tgagtctcaa taaaggatat tatcaaaaac   6780
tttattgaat agtatattct atttttgtct taaatgttta tatttattat tgatctttgg   6840
tttcaatatt actcttgatg atttgtttaa tcatatcctg gacaatttta cattcctaca   6900
ttgagagggt tgttttcaca caactgtcaa ggcagtatct ctgttaatag tgttagtatt   6960
taaaaatata attaaaaaat atttaaaata ttagaaataa aattaaaata aattaaacgt   7020
ctagtgtatt ttttaatttt ttttttcaaa tttttagaca aaatatatat tttatccgtt   7080
actttattgt gatcaagttt catttgggtt caaaattctc tttctatgtc tattatagtc   7140
aatttaaact atgaaattta tttcatcaaa tgtatttatt gaaagttatt tatcgtttga   7200
tttatcgaat atatgtatta cagttttaag aagttatttt tcaaaagaga attttgataa   7260
actgcgggaa aaaataaaac ctttatccga ttttgttttt ggcgaaaaat taacgctttt   7320
ggttgggctt gtgttccatt ttcgttctaa ctaaagaaat tctttactac attgtaggcc   7380
caagacctaa tcccaataac gtagtgatat ttttttcaaa ttattatatt tccacatgaa   7440
aagcccattt atccgaaggt cataagaata actaaagtat acccaaaaaa aaaaacctaa   7500
aaattattcc ctgaccaaaa aaaaaatcta aaattattct aaataaagac caaaaataaa   7560
```

```
tattcaaaag agagagaaaa ttaaagaatt ttacattttc gcaatcacaa agaaaaaacc   7620

caaaagcgta aactttatca cacatgcaca aaagaaaaaa cttcgtattt gttattcaaa   7680

aaatgttcta taaatattaa atatcattct atatgtattt gtgtatatat atatgttgtt   7740

tcacacattt ttaacaaaat aagtcactgg aatagtcaat tattttttag caaaataatg   7800

aaatttttta tgaatactaa atatatatat ttttaaatat gtaacaactg attttgtgtc   7860

tattaagcat ggttattaac tattagttta tattttttag gtaataaact ttttttgata   7920

aataattagc aaacaaaata atagaagcac aatggttaag ggtttgaact attattatca   7980

aatttttttg tgtatagtag tttatgtatt tttagctagg agttgtagga ctaagatcat   8040

gattggctat tattagatct aaatttatga taagtgcaac aaactatttt tgttgatggc   8100

atagtgtgtg caaagaaaaa aatcagaaga gcgatgggac aaacagagag acacaacatt   8160

atcccctagt ccaagtaacc aaagttctgt tcttgtggag actgaattgt tcattggact   8220

tcccgaatgg cgctaggcgc tagttacact accctaaact gtttagcggc gcccaatcta   8280

gtcgcgggtg actaactgcc gccaagccat tttgtggcgg ttcaaaccgc tactaaattc   8340

tctcagaacc gctgcaatct gccggttttc gtgtagtgat gcaacatatt atattaactc   8400

actagtattg tactatcatt ttggaagaaa agaagatcat cctcaataat gtgtcataaa   8460

tcatgctttc atttcctagt gatgaagaaa aaatgtagta tatatatata tatgccgcgt   8520

ttattatttg ctaaaatttt tcattgttac tacctaggtc tgttttgatt tcctccctat   8580

ttttgttgta agttttaagt aaccaaggac agacataata aaaacaaggt gtgttgtatc   8640

gtattattgt atgtacctat gtatgcttac atgatgatta tattatttgt cacgtccatt   8700

atatattctc tctctctcta tactttggca acccttgaag caagacagaa ttattaatgt   8760

ttgttcacta aaacttggta ctagaaaact taacttggtt gatacgtgtt gatgtgtgtg   8820

tgtgtgttga tgtgttggtg tgtgttggtg tgttggtca                          8859
```

<210> SEQ ID NO 2
<211> LENGTH: 8688
<212> TYPE: DNA
<213> ORGANISM: Arachis hypogaea L. variety Shitouqi
<220> FEATURE:
<221> NAME/KEY: misc_feature
<222> LOCATION: (1)..(8688)
<223> OTHER INFORMATION: Genomic nucleotide sequence of LBA5b-1 from Shitouqi

<400> SEQUENCE: 2

```
aagaagaaga tggtgagagg aaagattgag atgaaaagga tagagaatgc aacaagccgt     60

caagtaacgt tttcaaagag gaggagtggg cttctaaaga aagcacatga gctttctgtt    120

ctttgtgatg cacaaattgc tcttataatc ttttcacaaa gtgggaggct ctttgaatac    180

tcaagtatac ttcagagtaa gcccttactt aatcacttta ttttcttgct tcatcaacat    240

tcatgttagt gttagtttca ttctttaatt tttattcttc tcctaattaa ttagtacaat    300

actactactt attattgaac tattatatat atggtttaat cttggagaaa ctaaaggttt    360

actttaattt gctcaaacta tgatacatgt gttttgttgt gagttgcgct aagtcttcct    420

caaactacct agatttgatg atcaaagaac atggatctca ttgaaaaaaa agtgtgtggc    480

tttccgttta tggtaagcta actactactg gtaattacaa aagtatatac actaatttag    540

aaatactcaa cacttgctaa attgtagtag tagcatttgg ttgctgaata aattggaact    600

tgaaatactc tgctatgtaa ttatttcaat gctctccgta tcaaataagg taaaaaaaaa    660
```

```
atggtttttt aaaatttttt ctaagatatt atatagtgta tttttcatta tacatgtttt    720
aagtgagatt aagaaaaaaa tatgtgaaga gcaaagatat attgtagtat tacaaaagac    780
catcaccttt tgcaacatta cttaagaaaa aaaaaaacct aagattacct atttttattt    840
gatgttgagt ttagttctgc aatctgctct gtactaatta tatctttatc ctaaatataa    900
caaagaggag tgctaagggg ccagcagatt ttgtgagttg tagccatcaa ttagtcatca    960
atagtgtatt taatggtgtg agatttcatc taacggtgga gaatcactct tttttttttt   1020
gctggctaag tattggccag attttaataa atctgctggc ccctagactt ttcctataac   1080
gaatgctgca ttctttttcc tttttttttt cttttctccc ctataatttg ctagattatc   1140
attgatcctt attatgaaat tatttatttc aaagagacac atgcaagagt ctcttgagtt   1200
tttaagttga aaagtgaatt atggataggt cttttttgtt ttatattaaa attctatttt   1260
ttgtttaaaa aaatgagagt aacaatttta taaaaaaagt aaaaactaac atggactaaa   1320
agtctgattg atttgtattt gtaatttttt tatttttaat actttgtgaa aaaatattaa   1380
ataaaaaact gtaaaattat atattttatt ttattttatt ttttacaaaa ttctttaaaa   1440
aatatgaaaa tagaattgca atgaacttgt aaactaatct cttttgtcct ttgttctgat   1500
ctcttattac ttcttgaata taaaaaaaaa aacactaact aaagtagtaa ttcacagaac   1560
tatagtacaa ttatctgcat tttttatgat aatagttcag gaaattgcat tctcatcacg   1620
tctttcgaat actaattgag acatacatgg tgggagtttt ggcagaacaa gaaagggggg   1680
aacatgttca ggtgctgcca tgtgttcatg cggtttattt ttcccatgac caactttgct   1740
cattctaaat tcctttcttt aaacactttt tttttttaat ataatttaga aaaaactttc   1800
aagtataccc gtatattagt gttttagtca tttttaacgg ttgatcttaa ttatatatta   1860
tatatatttt ttgtaattaa gatcaacggt taaaaattat taaaacacca ttatacttgt   1920
acactttaaa gtttttctat aacttatttt atggcaataa cacatctatg tatatatatg   1980
tcttttccta acctaggaac tgggaagata ttgtagctat cttttttttt ttttttaact   2040
cttaatagtg tgttttgatt ttggctctgc tagttagtag caatgaagaa gttctatgaa   2100
gctataatat cttcaaaaaa gattatacaa tagaaataga atagtgggtg tagataggcc   2160
tacaatgggt atgtagcagc aagatttcca aatctagggt tttgacatat acatttccta   2220
tctcaataga tcttcaatta agaggctata taatctaaat gttgcaatgt agggtttgta   2280
gccttgaagc acatgcatat ttcatttatt tgcttctctt ttattgtatt atgttttctt   2340
ttgttaattg aatgaaggaa tttttgttag atagtatata tgtacttaaa tgcaaggcta   2400
aatattcata tttactttag atgaatataa aattaaatct gatgaatttc tccttgtttt   2460
tgtctgaaat tcaactcatg tatagtcaga ctattttctg tatgataggt gaacatatat   2520
atatttttaa aaaataatat tatgtacata caaaaattaa tcaccaaatt agttatcatg   2580
tagttagata tatttaaaca tgttacatac attttcaatg tgtatttatg agtagttgat   2640
ttgactattg atttttagtg tgcatttagt gcagttattt ttcctcagtg aattgatttt   2700
catttttttg taatttaaat gttatattta agcatttaat attaattttg gaaaataaaa   2760
aatgaaccca taagatgtga taaatcgcaa atcttgaatg caaaaggcta gttttttttt   2820
ttttttaagc cctaattatc atagcaagta aacaggttaa tccaataggt ttatgtcatt   2880
tagtgcatgg tgggtcaata gatccctgtt ttttcaactc atgatgtaat aatactcctt   2940
attttcacat tttatgctcc aacttttgta tctcataaca ttcatgtaga aaatatggat   3000
```

```
taacctgaac ttggagattt ttttaaaaaa aaaatcatat taattaactg tatatcttca   3060
tcataggaat gcctgcaaag ttttttgctg acattaatga ataatataat gttctgattg   3120
ctttgttttc aatagctacc tcttaacagt atatgttttt aatttctttg aaatgtttca   3180
gcatggaaca aatgttggaa cgctaccgtc aatatgtagc agatgatggt cgtatcaata   3240
atattggaga attccaggta tagtaaagag aatatctata atggtatagt taagttacca   3300
tttaccgcta cgataccaac agtatttctg tcaacttctg ctaactttta tttataactg   3360
tgtttaatgg aagtgttttt ctggatgtgt ctaataaaaa tgtctttttt atgactgagt   3420
ctaataaaag tgtttttata aatgtatttt ttggatgtgt ctttttatac atgtgcttaa   3480
aatataataa ttaattattg ttggcaataa attgacagat aacctattgg taccctatat   3540
ttttccttta ccaatatata taatatatat tgactataat accttttagt tcttttaaaa   3600
tttcaggatt atttaataat atatagtttt atttatttgt agtatgaaaa cctatatata   3660
tttcatcaag acaactattt ggagctagca gctagctact cctaataagt aataagcatg   3720
cgatattgat attcatagca catttaattt gataagaaag tgaagattat taataacaca   3780
cgaccagatc aatatataat attcatgtca tgccatgcta ttaatttttt gggattatta   3840
aagatataac tatttatgta attttttcgt caatttaagt ttttagaaaa agtagtttca   3900
ttagatggta taagagttta ttggcatcta gagtaaataa atttattaat gtggctgttt   3960
tattattata cttcctcctt cttaaattat ctgattcttt ttaatttttt tatttttgtt   4020
acatttttag ttttaagaag ttattaatta atttgtttca ctataaatta aaaaagttag   4080
aagaatagaa ttatgaatgg aaagagaaat taatattaag aacatttttc tttttttttg   4140
tttgttcttt acattttttt ataaaattta atgattattt tagtaattat ataattaaaa   4200
agagacagat aggtaagagt aacgttttat atatagtaaa aattaaatta taatggattg   4260
taataaaatt ggttttatgc tttgacatgc agcaattgga atttgatccc ccaagcttgg   4320
ctaagaagat tgaacttctt gagctttctc aaaggtcaat cctgtgttta aatactaatc   4380
cgtttattgc tgttgttcat attctaatac tgagtattat attcattaat atttggtgtg   4440
ccatgaaatt ttaattcatt gtttgaattt gttaggaagc taatgggaca gggcctgagc   4500
tcttgttcat ttgatgaact cgttggaatt gagaatcagc ttgtgtcaag cttgcaaaac   4560
attaggctca aaaaggtcat taataattca caacattata ttatattata tagatgtata   4620
tatatataag aacaagacgt tcttaattta attaatttaa tgtactttca ggctcagctt   4680
tatagagagc atattgaaca actacaaaat aaggtacctg agcttagttt ggatgcaaat   4740
tatacatctt taaagaatta aaaaaaattg tataaattat tttaattagg tttcatggtg   4800
gacatctgac acatttttat gtattgaatc caggagaagg atttgctcct agagaatgcc   4860
aaattaactg aaatggtgag ttaccatttt cttttcatga tttatagctg gtttgacaaa   4920
tttatttaga aagttattta taattttatt gtgtttggta aataaaaaaa taatgcgatt   4980
gtatttgtag ttttaaaaag tttgaagtat tttgaaacaa aaatattatg tttacactaa   5040
aaattcgtta ttaaataagt ttttatgtat ttgtatataa ataaatatgt agtttaattt   5100
atttttaatg agtttagtag cttatttttg tagatattta gtatggttga ttttgaaagc   5160
acttaagaaa atatttttta aagttagttt gtgtttatta aaattaaaat gtataatata   5220
tatttatata ttaataaata tttaaattta ttcttatatt aaaaagtata atttttgtct   5280
ctaaaatttt caaaatatct gtaacgtaaa atttgtttca attttgtttc taacatttta   5340
aatatatttc aattatacct ttgagggtag gggtggcaat cgaggaagtc cgctccgtca   5400
```

```
aaagcccgcc atctggtggg tctactaaat ctcttttttt tttttttatg aactattaaa   5460
tattaaataa tatatataat ttcataacta ttttaataaa tttataattt ctaaatctac   5520
aaacaataaa gtcttcataa ttataaatat ataataaaca taattataaa taaaattttt   5580
tgaaacaaaa tataaacatt gttcaaaata tataattaaa catcttcaaa tttataatca   5640
atcaaatata aaacataatc caaaatataa tttagaacat ctttaattat ctacaacctc   5700
ttgtgtttgt aaaaaaatgt ccttgaccaa aaagacgcct ggttcggtgg ggaagcccgc   5760
tccgtcctgt caaaatccac ggattaagcg atgcgggtta gacagatttt taggtttgac   5820
ggttttaaat tttcagtcgt tcaacccgtc tttttagtg ggttatacgg actaatctga   5880
tgaattttgg cccgtttgtc acctcttttt gagggttaac actattaatg gagatgctat   5940
tgtgacaatt atgtgctgac atgtcactaa aacgtggtaa aactcagcta ttaacatgtc   6000
agggtagtac tgtcatgtta tttgttatcc aactaaggaa tataattgaa atataaaaaa   6060
ccaagttgag ttggtctagt ggtgagctca ttggtttgct taaacaagtg ttttaaatcc   6120
cgccttgtgc atgcagcaac ctattggcca gtgacaaacc cttaaatgga gcttagtact   6180
gaggcggatt agtccttggc ctaccgggtt ggaggatacc gtggccaagg ataccgtgga   6240
aaaaaaaaag aaatataaaa agtaaaatta aaactaaatg ttaaaagata aaatgtgaac   6300
attgaggata aaaatagaat ttattactct attattttta aataaaaaat atattaataa   6360
tattcttaaa atatatcagg tttattgaga tttattttaa tacaataata tttttactaa   6420
aaaattatga taagaactac atattcttct tacaaaatta taaaaaatat tttaaaaatg   6480
tatcattttt aatacataaa aatagctttg atacctttaa aaatttcttt agtaatactt   6540
ttaataattt gctaacaaac atgtgattat gacaactaat taagtattat atagacttat   6600
tagtaaatta tataaaaata ttttaaaaag tatccaagtg atttttatat aataaaagtt   6660
atatttttta aaatattttt atataatttt ctaaaatttt atagtattta taaaaagatt   6720
tattttcaat aaaagatatt attatattaa aatgagtctc aataaaggat attatcaaaa   6780
actttattga atagtatatt ctatttttgt cttaaatgtt tatatttatt attgatcttt   6840
ggtttcaata ttactcttga tgatttgttt aatcatatcc tggacaattt tacattccta   6900
cattgagagg gttgttttca cacaactgtc aaggcagtat ctctgttaat agtgttagta   6960
tttaaaaata taattaaaaa atatttaaaa tattagaaat aaaattaaaa taaattaaac   7020
gtctagtgta tttttttaatt tttttttca aattttttaga caaaatatat attttatccg   7080
ttactttatt gtgatcaagt ttcatttggg ttcaaaattc tctttctatg tctattatag   7140
tcaatttaaa ctatgaaatt tatttcatca aatgtattta ttgaaagtta tttatcgttt   7200
gatttatcga atatatgtat tacagtttta agaagttatt tttcaaaaga gaattttgat   7260
aaactgcggg aaaaaataaa acctttatcc gattttgttt ttggcgaaaa attaacgctt   7320
ttggttgggc ttgtgttcca ttttcgttct aactaaagaa attctttact acattgtagg   7380
cccaagacct aatcccaata acgtagtgat attttttttca aattattata tttccacatg   7440
aaaagcccat ttatccgaag gtcataagaa taactaaagt atacccaaaa aaaaaaacct   7500
aaaaattatt ccctgaccaa aaaaaaaatc taaaattatt ctaaataaag accaaaaata   7560
aatattcaaa agagagagaa aattaaagaa ttttacattt tcgcaatcac aaagaaaaaa   7620
cccaaaagcg taaactttat cacacatgca caaaagaaaa aacttcgtat ttgttattca   7680
aaaaatgttc tataaatatt aaatatcatt ctatatgtat ttgtgtatat atatatgttg   7740
```

```
tttcacacat ttttaacaaa ataagtcact ggaatagtca attatttttt agcaaaataa   7800

tgaaattttt tatgaatact aaatatatat atttttaaat atgtaacaac tgattttgtg   7860

tctattaagc atggttatta actattagtt tatatttttt aggtaataaa cttttttttga  7920

taaataatta gcaaacaaaa taatagaagc acaatggtta agggtttgaa ctattattat   7980

caaatttttt tgtgtatagt agtttatgta tttttagcta ggagttgtag gactaagatc   8040

atgattggct attattagat ctaaatttat gataagtgca acaaactatt tttgttgatg   8100

gcatagtgtg tgcaaagaaa aaaatcagaa gagcgatggg acaaacagag agacacaaca   8160

ttatccccta gtccaagtaa ccaaagttct gttcttgtgg agactgaatt gttcattgga   8220

cttcccgaat ggcgctaggc gctagttaca ctaccctaaa ctgtttagcg gcgcccaatc   8280

tagtcgcggg tgactaactg ccgccaagcc attttgtggc ggttcaaacc gctactaaat   8340

tctctcagaa ccgctgcaat ctgccggttt tcgtgtagtg atgcaacata ttatattaac   8400

tcactagtat tgtactatca ttttggaaga aaagaagatc atcctcaata atgtgtcata   8460

aatcatgctt tcatttccta gtgatgaaga aaaaatgtag tatatatata tatatgccgc   8520

gtttattatt tgctaaaatt tttcattgtt actacctagg tctgttttga tttcctccct   8580

atttttgttg taagttttaa gtaaccaagg acagacataa taaaaacaag gtgtgttgta   8640

tcgtattatt gtatgtacct atgtatgctt acatgatgat tatattat               8688
```

<210> SEQ ID NO 3
<211> LENGTH: 8043
<212> TYPE: DNA
<213> ORGANISM: Wild diploid A. duranensis
<220> FEATURE:
<221> NAME/KEY: misc_feature
<222> LOCATION: (1)..(8043)
<223> OTHER INFORMATION: Genomic nucleotide sequence of LBA5a

<400> SEQUENCE: 3

```
aagaagaaga tggtgagagg aaagattgag atgaaacgga tagagaatgc aacaagccgt     60

caagtaacgt tttcaaagag gaggagtggg cttctaaaga aagcacatga gctttctgtt    120

ctttgtgatg cacaaattgc tcttataatc ttttcacaaa gtgggaggct ctttgaatac    180

tcaagtactt cagagtaagc ccttacttaa tcactttatt ttcttgcttc atcaagattc    240

atgttagtgt ttcattcttt ttattcttct cctaattaat tagtacaata ctactactta    300

tatattatat ggtttaatct tggagaaact aaaggcttac tttaatttgc tcaaactatg    360

atacatgtgt tttgttgtga cttgtgctaa gtcttcctca aattaaacta cctagatttg    420

atgatcaaag aacatggatc tcattaaaaa aaagtgtgtg gctttccgtt tatggtaagc    480

taactactac tggtaattac aaaagtatat acactaattt agaaatactc aacacttgct    540

aaattgtagt acttagcatt tggttgctga ataaattgga acttggaata ctctgctatg    600

taattatttc aatgctctcc taatcaaata aggtcaaaaa aatggttttt aaaatttttt    660

tttctaagat attatatagt gtatttttca ttatacatgt tttaagtgag attaagaaaa    720

aaatatgtga agagcaaaga tatattgtat tacaaaagat catcaccttt tgcaacaata    780

cttgagaaaa aaaaaaccta agatgaccta tttttattga tgttgagtta agttctgcaa    840

tctgctctgt actaattata tctttatcct aaatataaca agtgctgcat tccaatatat    900

acattgttga aatcaccaca agccaataat ctgacctact cttaaaagta aggggtaaga    960

aaccttatat aatatataca caacttttct tgtttttttt tttttctata atttgctaga   1020

ttatcattga tccttattat gaaattattt atttcaaaga gacacatgca agagtctctt   1080
```

```
gagtttttaa gttgaaaagt gaattatgga taggtctttt ttgttttata ttaaaattct   1140
atttttgtt taaaaaaatg agagtaacaa ttttattttt atttaaaatt aaactgagag   1200
taacaatgat taaacgttat tttttaatta tagaaatttt aacatattat gatttttttg   1260
tccaaaaaat ttaaactttt aaataaaaaa cataaataat atataacaat gcttacaaga   1320
gaaggaaaat gtagattaaa aagggaaaaa aagtaaaaaa ttctaccatt ccataggata   1380
tataacacca aactacttca aaaactaaca tggactaaaa gtctgattga tttgtatttg   1440
taatttttta tttttaatac tgtgtgaaaa aatattaaac aaaaaactgt aaaattatat   1500
attttatttt attttttaca aaattcttta aaaaatatga aaatagaact gcaatgaact   1560
tgtaaactaa tctcttttgt cctttgttct gatctcttat tacttgaata taaaaaaaac   1620
actaattaaa gtagtaattc atagaactat agtacaatta tccgcatttt ttatgataat   1680
agttcaggaa attgcattct catcacgtct ttcgaatact aattgagaca tacatggtgg   1740
gagttttggc agaacaagaa aggggggaac atgttcaggt gctgccatgt gttcatgcgg   1800
tttattttc ccatgtccaa ctttgctcat tctaaatttc tttctttaaa cacttgtttt   1860
ttttaatata atttagaaaa actttcaagt ataccaatat actagtgttt tagtaatttt   1920
taacagttga tcttaattat atcttatata tattttttgt aattaagatc aacggttaaa   1980
cattattgaa acacgagtat acttgtacac tttaaagttt tcctataatt tattttatgg   2040
caataacaca tctatgtata tatgtctttt cccaacctag gaactgggaa gatattgtag   2100
ctatcttttt attttataac tcttaatagt gttcactatt aattcagttc cgtactacat   2160
tgtgtgtttt gattttggct ctgctactta gtagcaatga agaagttcta tgaagctata   2220
atatcttcaa aaaagatcat acaatagaaa taaaatagtg ggggtagata ggcctacaat   2280
gggtatgtag cagcaagatt tccaaatcta gggttttgac atatacattt cctatctcaa   2340
tagatcttca attaagaggc tatataatct aagtgttgca atgtaggctt tgtagccttg   2400
aagcacatgc atatttcatt tatttgcttc tcttttattg tattatgttt tctttcgtta   2460
attgaatgga ggaaattttg ttagataata tatatgtact taaatgcaag gctaaagtat   2520
tcatatttac tttagaggaa tataaaatta aatctgatga atttcttctt gtttttgtct   2580
gaaattcaac tcatatagtc agactatttt ctgtatgata ggtggaacat atataatttt   2640
taaaacataa tattataata aaaatgaatc accaaatcag ttatcatgta attggatata   2700
tttaaacatg tttcatacat tttcaatgtg tatttttgag tagttatttt tcctcagtga   2760
attgattttc ttttttgta atttaaatgt tatatttaag catttaatat taatttttga   2820
aaataaaaaa tgaacccata agatgtgata aatcacaaat cttgaatgta aaaggctagt   2880
tttttttaa aaggttagaa tctacacatt tagatttagc cctaattatt ataacaggtt   2940
aatccaatag gtttagccgt ttaggtcatt cagtgcatgg tgggtcaata gatccctgtt   3000
ttttcaactc atgctgtaat aatatactcc ttattttcat attttatgct ccaacttttg   3060
tatctcataa cattcatgga gaaaaaatgg attaacctga acttggagaa ttttttttta   3120
atcgtattaa ttaactgtat atcttcatca taggaatgcc tgcaaagttt tttgctgaca   3180
ttaattaata atataacgtt ctgattgctt tgttttcaat agctaccttt aattttgcac   3240
taatattaac aactcacagt atatattttt aatttctttg aaatgtttca gcatggatca   3300
acttttggaa cgctaccgtc aatatgtagc agatgatggt cgtatcaata atattggaga   3360
attccaggta tagtaaagag aatatctata atggtataat aattaagtta ccatttacca   3420
```

```
atatatataa tatatattga ctataatacc ttttagttct tttaaaattt caggactatt   3480
ttataatata tagttttatt tatttgtagc atgaaaacct atatatttca tcaagacaac   3540
tatttggagc tagcagctag ctactcctaa taagtaataa gcatgcgata ttgatattca   3600
tagcacattt aatttgatat gaaagtgaag attattaata acacacgacc cgaccaatat   3660
atgatattca tgtcatgcca tgccattaat tttttgtgat tattaaagat ataactattt   3720
atgtattttt tcgtcaattt aagtttttag aaaaagtagt ttcattagac ggtataagag   3780
tttattggca tctagagtaa ataaatttat taatgtggct gttttgtatt attatacttt   3840
ctccttcttt aattatctga ttcttttta tttttttatt ttgttacatt tttagtttta   3900
aggagttatt aattaatttt ttttcattat aaataaaaaa agttagaaga atagaattat   3960
gaatggaaag agaaagtaat attaagaata ttttatatat agtaaaaatt aaattataat   4020
ggattgtaat aaaattgttt tatgctttga catgcagcaa ttggaatttg atcccccaag   4080
cttggctaag aagattgaac ttcttgagct ttctcaaagg tcaatcctgt gtttaaagac   4140
taatccgttt attgctgttg ttcatattct aatactgagc attatattca ttaatatttg   4200
gtgtgccatg aaattttaat tcattgtttg aatttgttag gaagctaatg ggacagggcc   4260
tgagctcttg ttcatttgat gaactcgttg gaattgagaa tcagcttgtg tcaagcttgc   4320
aaaacattag gctcaaaaag gtcattaata atttacaaca ttatattata ttatatataa   4380
atataagaac aagacgttct tgatataatt taatgtattt tcaggctcag ctttatagag   4440
agcatattga acaactacaa aataaggtac ctgagcttag tttggatgca aattaaatga   4500
tacatcttta aagaattgaa aaaatgatgt ataaattatt ttaattaggt ttcatggtgg   4560
acatctgaca catttttatg tattgaatcc aggagaagga tttgctcctg gagaatgcca   4620
aattaactga aatggtgagt taccattttc ttttcatgat ttatagctgg tttgacaaat   4680
ttatttagaa aggtatttat aattttattg tgtttggtaa ataaaaaaat aatacaagtt   4740
agaagtattt tgaaacaaaa atattatgtt tacactaaaa attcgttatt aaatcaggtt   4800
ttatgtattt atatataaat aaatatgtag tttaatctat ttttaatgat tttagtagct   4860
tatttttgta tatatttagt atggttgatt ttgaaagcac ttaagaaaat attttttaaa   4920
gttggtttgt gtttattaaa attaaaatat ataatatata tttatatatt aataaatatt   4980
taaatttatt ctcatattaa aaagtataat ttttgtctct aaaattttca aaatatctgc   5040
aaggtttaat ttgtttcaat tttgtttcta acattttaaa tatgtttcaa ttatacgttt   5100
gagggtaggg gtggcaatcg agagaaccta caagatggca ggcctgctaa atctcttttt   5160
tttatgaatt attaaatatt aaataatata tataattttt caaccatttg aataaattta   5220
taatttctaa agacaaaaaa agttttaatt tctaaattta caaacaataa agtctttata   5280
attataaata tgtaataaac ataattataa ataaagtttt ttgaaacaaa atataaatat   5340
tgttcaaaat atataattaa acatctttaa gtttataatc aatcaaatat aaaatataat   5400
ttaaaatata atttagaaca tttttaatta ttcacaacct cttgtagatc aataacactg   5460
taaaaattta taaaaaaatg gccttgacca aaaagacgtc tggttcggtg ggacctgtcc   5520
tgtcaaaatt tacggattaa gcggtacgag ttagacatac ttttttaagt ttgacaattt   5580
caaattttca gtcaaattcg tctttttaa tgggttatgt gggctaagct gacgggttta   5640
cctctatttg agggttaaca ctattaatag agatgctatt gtgacaatta tatgctgacg   5700
tgtcactaaa acggggtaac tctcagctat taacatgtca gggtagtatt gtcatgttat   5760
ttgttaccca actaaggaat ataattgaaa tatattgaaa tataaaagga aaaattgaaa   5820
```

```
ctaaatgtta aagataaaat gtgaatattg aggataaaaa tagaatttat tactctatta   5880
tttttaaat aaaaaatata ttgataatat tcttaaaata tatcaggttt attgagattt   5940
attttaatac aataatattt ttactaaaaa aattatgata agtaccacat attcttctta   6000
aaaaatgtat catgtttaat acataaaaat agctttgatg cctttaaaaa tttctttagt   6060
aatactttta ataatttgct aacaaacatg tgattatgac aactaattaa gtattatatt   6120
gtcttattag taaattataa aaaaattatt tttaaaagta ttcaagtgat ttttatataa   6180
taaaagttat atttttaaa atatttttat ataattttct aaaattttat agtatttata   6240
aaaaaaatat tttcaataaa agatattatt atattaaaat gagtctcaat aaaggatatt   6300
atcaaaaact ttattgaata gtatattcta ttttaatttg tcttaaatgt ttaaatttta   6360
ttttaatttt attattgatc tttggtttca atattactca tgatgatttg tttaattata   6420
tcctggacaa ttttacattc ctacattgag agggttgttt tcacacaatt gtcaaggcag   6480
tatctctgtt aatagtgtta atatctaaaa atgtaattaa aaaatattta aaatattaga   6540
aataaaatta aaataaatta aacgtctagt gtattttttt aattttttt caaattttta   6600
gacaaaatat atactttatc cattaattta ttgtgatcaa gtttcatttg ggttcaaaat   6660
tctctttaat ttattgtgat caagtttcat ttgggttcaa aattctcttt ctatgtctat   6720
tataatcaat ttaagctatg aaatttattt catcaaatgt atttattgaa agttatttat   6780
cgtttgattc atcgaatata tatattacag ttttttttt tttgatgata tgtattacag   6840
ttttaagaag ttattttttt caaaagagaa ttttgataag ctgcgtgaaa aataaaaccg   6900
ttaactaaag aaatgctcta ttacattgta ggcccaagac ctaaacccaa taacgtagtg   6960
atagtgttta catttttttc aaattattat atttccacat gaaaagccca tttatccgaa   7020
ggtcataaga ttattccctg acaaaaaaaa tctaaaatta ttcaaaataa agaccaaaaa   7080
caaatattca aaagaaagag aaaaacccca aaagcataaa ctttatcata catgcacaaa   7140
agaaaaaact tcgtatttgt tattcaaaaa tgttctgtaa atattaaata tcattctata   7200
tgtatttgtg tatttatatg tttcacgcat ttttaacaaa ataagtcact ggaatagtca   7260
attatttttt agcaaaataa tgattttttt tgtgtgtgta ttgttagcta ggagttgtag   7320
gactaagatc atgattggct attattagat ccaaatttat gataagtgca acaaactatt   7380
tttgttgatg gcatagtgtg tgcaaagaaa aaaatcagaa gagcaatggg gcaaacagag   7440
aggcgcaaca ttatccccta gtccaagtaa ccaaagttct gttcttgtgg agactgaatt   7500
gttcattgga cttcctgaat ggcgctaggc gctaactaca ttaccctaaa ctgtttagcg   7560
gcgcccaatc tagtcgtggg tgactaactg ccgccaagcc gttttgtggc ggttcaaacc   7620
gctacgaaat tctctcagaa ccgctgcaat ctgccggttt tcatgtagtg ctagtgcaac   7680
atattatatt aattcactag tattgtacta tcattttgga agaaaagaag atcatcctca   7740
ataatgtgtc atatatcatg ctttcatttc ctagtgatga agaaaaaatg tagtatatat   7800
atatatatat gccgcgttta ttatttgcta aaatttttca ttgttgttac ctaggtctgt   7860
tttgattccc tccctattct tgttgtaagt tttaagtaac caaggacaga cagacatatt   7920
aataaaaaca aggtgttgta tcattattgt gattacatta ttgtatcatt tgtaatttat   7980
gtaaccaagg acagacagac atattaataa aaacaaggtg ttgtatcatt tgtaatttat   8040
gta                                                                 8043
```

<210> SEQ ID NO 4

<211> LENGTH: 8098
<212> TYPE: DNA
<213> ORGANISM: Arachis hypogaea L. variety Tifrunner
<220> FEATURE:
<221> NAME/KEY: misc_feature
<222> LOCATION: (1)..(8098)
<223> OTHER INFORMATION: Genomic nucleotide sequence of LBA5a

<400> SEQUENCE: 4

```
aagaagaaga tggtgagagg aaagattgag atgaaacgga tagagaatgc aacaagccgt     60
caagtaacgt tttcaaagag gaggagtggg cttctaaaga aagcacatga gctttctgtt    120
ctttgtgatg cacaaattgc tcttataatc ttttcacaaa gtgggaggct ctttgaatac    180
tcaagtactt cagagtaagc ccttacttaa tcactttatt ttcttgcttc atcaagattc    240
atgttagtgt ttcattcttt ttattcttct cctaattaat tagtacaata ctactactta    300
tatattatat ggtttaatct tggagaaact aaaggcttac tttaatttgc tcaaactatg    360
atacatgtgt tttgttgtga cttgtgctaa gtcttcctca aattaaacta cctagatttg    420
atgatcaaag aacatggatc tcattaaaaa aaagtgtgtg gctttccgtt tatggtaagc    480
taactactac tggtaattac aaaagtatat acactaattt agaaatactc aacacttgct    540
aaattgtagt acttagcatt tggttgctga ataaattgga acttggaata ctctgctatg    600
taattatttc aatgctctcc taatcaaata aggtcaaaaa aatggttttt aaaatttttt    660
tttctaagat attatatagt gtatttttca ttatacatgt tttaagtgag attaagaaaa    720
aaatatgtga agagcaaaga tatattgtat tacaaaagat catcaccttt tgcaacaata    780
cttgagaaaa aaaaaaccta agatgaccta tttttattga tgttgagtta agttctgcaa    840
tctgctctgt actaattata tctttatcct aaatataaca agtgctgcat tccaatatat    900
acattgttga aatcaccaca agccaataat ctgacctact cttaaaagta aggggtaaga    960
aaccttatac aatatataca caacttttct tgtttttttt ttttctataa tttgctagat   1020
tatcattgat ccttattatg aaattattta tttcaaagag acacatgcaa gagtctcttg   1080
agtttttaag ttgaaaagtg aattatggat aggtcttttt tgttttatat taaaattcta   1140
ttttttgttt aaaaaaatga gagtaacaat tttattttta tttaaaatta aactgagagt   1200
aacaatgatt aaacgttatt ttttaattat agaaatttta acatattatg atttttttgt   1260
ccaaaaaatt taaactttta aataaaaaac ataaataata tataacaatg cttacaagag   1320
aaggaaaatg tagattaaaa agggaaaaaa agtaaaaaat tctaccattc cataggatat   1380
ataacaccaa actacttcaa aaactaacat ggactaaaag tctgattgat ttgtatttgt   1440
aatttttat ttttaatact gtgtgaaaaa atattaaaca aaaaactgta aaattatata   1500
ttttatttta ttttttacaa aattctttaa aaaatatgaa aatagaactg caatgaactt   1560
gtaaactaat ctcttttgtc ctttgttctg atctcttatt acttgaatat aaaaaaaaca   1620
ctaattaaag tagtaattca tagaactata gtacaattat ccgcattttt tatgataata   1680
gttcaggaaa ttgcattctc atcacgtctt tcgaatacta attgagacat acatggtggg   1740
agttttggca gaacaagaaa ggggggaaca tgttcaggtg ctgccatgtg ttcatgcggt   1800
ttatttttcc catgtccaac tttgctcatt ctaaatttct ttctttaaac acttgttttt   1860
tttaatataa tttagaaaaa ctttcaagta taccaatata ctagtgtttt agtaattttt   1920
aacagttgat cttaattata tcttatatat attttttgta attaagatca acggttaaac   1980
attattgaaa cacgagtata cttgtacact ttaaagtttt cctataattt attttatggc   2040
aataacacat ctatgtatat atgtcttttc ccaacctagg aactgggaag atattgtagc   2100
```

```
tatcttttta ttttataact cttaatagtg ttcactatta attcagttcc gtactacatt   2160
gtgtgttttg attttggctc tgctacttag tagcaatgaa gaagttctat gaagctataa   2220
tatcttcaaa aaagatcata caatagaaat aaaatagtgg gggtagatag gcctacaatg   2280
ggtatgtagc agcaagattt ccaaatctag ggttttgaca tatacatttc ctatctcaat   2340
agatcttcaa ttaagaggct atataatcta agtgttgcaa tgtaggcttt gtagccttga   2400
agcacatgca tatttcattt atttgcttct cttttattgt attatgtttt ctttcgttaa   2460
ttgaatggag gaaattttgt tagataatat atatgtactt aaatgcaagg ctaaagtatt   2520
catatttact ttagaggaat ataaaattaa atctgatgaa tttcttcttg tttttgtctg   2580
aaattcaact catatagtca gactattttc tgtatgatag gtggaacata tataattttt   2640
aaaacataat attataataa aaatgaatca ccaaatcagt tatcatgtaa ttggatatat   2700
ttaaacatgt ttcatacatt ttcaatgtgt atttttgagt agttattttt cctcagtgaa   2760
ttgattttct ttttttgtaa tttaaatgtt atatttaagc atttaatatt aatttttgaa   2820
aataaaaaat gaacccataa gatgtgataa atcacaaatc ttgaatgtaa aaggctagtt   2880
ttttttttaaa aggttagaat ctgcacattt agatttagcc ctaattatta taacaggtta   2940
atccaatagg tttagccgtt taggtcattc agtgcatggt gggtcaatag atccctgttt   3000
tttcaactca tgctgtaata atatactcct tattttcata ttttatgctc caacttttgt   3060
atctcataac attcatggag aaaaaatgga ttaacctgaa cttggagaat ttttttttaa   3120
tcgtattaat taactgtata tcttcatcat aggaatgcct gcaaagtttt ttgctgacat   3180
taattaataa tataacgttc tgattgcttt gttttcaata gctaccttta attttgcact   3240
aatattaaca actcacagta tatattttta atttctttga aatgtttcag catggatcaa   3300
cttttggaac gctaccgtca atatgtagca gatgatggtc gtatcaataa tattggagaa   3360
ttccaggtat agtaaagaga atatctataa tggtataata attaagttac catttaccaa   3420
tatatataat atatattgac tataatacct tttagttctt ttaaaatttc aggactattt   3480
tataatatat agttttattt atttgtagca tgaaaaccta tatatttcat caagacaact   3540
atttggagct agcagctagc tactcctaat aagtaataag catgcgatat tgatattcat   3600
agcacattta atttgatatg aaagtgaaga ttattaataa cacacgaccc gaccaatata   3660
tgatattcat gtcatgccat gccattaatt ttttgtgatt attaaagata taactattta   3720
tgtatttttt cgtcaattta agtttttaga aaaagtagtt tcattagacg gtataagagt   3780
ttattggcat ctagagtaaa taaatttatt aatgtggctg ttttgtatta ttatactttc   3840
tccttcttta attatctgat tctttttat tttttattt tgttacattt ttagttttaa   3900
ggagttatta attaattttt tttcattata aataaaaaaa gttagaagaa tagaattatg   3960
aatggaaaga gaaagtaata ttaagaatat tttatatata gtaaaaatta aattataatg   4020
gattgtaata aaattgtttt atgctttgac atgcagcaat tggaatttga tccccaagct   4080
tggctaagaa gattgaactt cttgagcttt ctcaaaggtc aatcctgtgt ttaaagacta   4140
atccgtttat tgctgttgtt catattctaa tactgagcat tatattcatt aatatttggt   4200
gtgccatgaa attttaattc attgtttgaa tttgttagga agctaatggg acagggcctg   4260
agctcttgtt catttgatga actcgttgga attgagaatc agcttgtgtc aagcttgcaa   4320
aacattaggc tcaaaaaggt cattaataat ttacaacatt atattatatt atatataaat   4380
ataagaacaa gacgttcttg atataattta atgtattttc aggctcagct ttatagagag   4440
```

-continued

```
catattgaac aactacaaaa taaggtacct gagcttagtt tggatgcaaa ttaaatgata   4500
catctttaaa gaattgaaaa aatgatgtat aaattatttt aattaggttt catggtggac   4560
atctgacaca tttttatgta ttgaatccag gagaaggatt tgctcctgga gaatgccaaa   4620
ttaactgaaa tggtgagtta ccattttctt ttcatgattt atagctggtt tgacaaattt   4680
atttagaaag gtatttataa ttttattgtg tttggtaaat aaaaaaataa tacaagttag   4740
aagtattttg aaacaaaaat attatgttta cactaaaaat tcgttattaa atcaggtttt   4800
atgtatttat atataaataa atatgtagtt taatctattt ttaatgattt tagtagctta   4860
tttttgtata tatttagtat ggttgatttt gaaagcactt aagaaaatat tttttaaagt   4920
tggtttgtgt ttattaaaat taaaatatat aatatatatt tatatattaa taaatattta   4980
aatttattct catattaaaa agtataattt ttgtctctaa aattttcaaa atatctgcaa   5040
ggtttaattt gtttcaattt tgtttctaac attttaaata tgtttcaatt atacgtttga   5100
gggtaggggt ggcaatcgag agaacctaca agatggcagg cctgctaaat ctcttttttt   5160
tatgaattat taaatattaa ataatatata taatttttca accatttgaa taaatttata   5220
atttctaaag acaaaaaaag ttttaatttc taaatttaca aacaataaag tctttataat   5280
tataaatatg taataaacat aattataaat aaagtttttt gaaacaaaat ataaatattg   5340
ttcaaaatat ataattaaac atctttaagt ttataatcaa tcaaatataa aatataattt   5400
agaacatttt taattattca caacctcttg tagatcaata acactgtaaa aatttataaa   5460
aaaatggcct tgaccaaaaa gacgtctggt tcggtgggac ctgtcctgtc aaaatttacg   5520
gattaagcgg tacgagttag acatactttt ttaagtttga caatttcaaa ttttcagtca   5580
aattcgtctt ttttaatggg ttatgtgggc taagctgacg ggtttacctc tatttgaggg   5640
ttaacactat taatagagat gctattgtga caattatatg ctgacgtgtc actaaaacgg   5700
ggtaactctc agctattaac atgtcagggt agtattgtca tgttatttgt tacccaacta   5760
aggaatataa ttgaaatata ttgaaatata aaaggaaaaa ttgaaactaa atgttaaaga   5820
taaaatgtga atattgagga taaaaataga atttattact ctattatttt ttaaataaaa   5880
aatatattga taatattctt aaaatatatc aggtttattg agatttattt taatacaata   5940
atatttttac taaaaaaatt atgataagta ccacatattc ttcttaaaaa atgtatcatg   6000
tttaatacat aaaaatagct ttgatgcctt taaaaatttc tttagtaata cttttaataa   6060
tttgctaaca aacatgtgat tatgacaact aattaagtat tatattgtct tattagtaaa   6120
ttataaaaaa aattattttt aaaagtattc aagtgatttt tatataataa aagttatatt   6180
ttttaaaata tttttatata attttctaaa attttatagt atttataaaa aaaatatttt   6240
caataaaaga tattattata ttaaaatgag tctcaataaa ggatattatc aaaaacttta   6300
ttgaatagta tattctattt taatttgtct taaatgttta aattttattt taattttatt   6360
attgatcttt ggtttcaata ttactcatga tgatttgttt aattatatcc tggacaattt   6420
tacattccta cattgagagg gttgttttca cacaattgtc aaggcagtat ctctgttaat   6480
agtgttaata tctaaaaatg taattaaaaa atatttaaaa tattagaaat aaaattaaaa   6540
taaattaaac gtctagtgta ttttttaat ttttttcaa atttttagac aaaatatata   6600
ctttatccat taatttattg tgatcaagtt tcatttgggt tcaaaattct ctttaattta   6660
ttgtgatcaa gtttcatttg ggttcaaaat tctctttcta tgtctattat aatcaattta   6720
agctatgaaa tttatttcat caaatgtatt tagtgaaagt tatttatcgt ttgattcatc   6780
gaatatatat attacagttt tttttttt ttgatgatat gtattacagt tttaagaagt   6840
```

```
tatttttttc aaaagagaat tttgataagc tgcgtgaaaa ataaaaccgt taactaaaga   6900
aatgctctat tacattgtag gcccaagacc taaacccaat aacgtagtga tagtgtttac   6960
atttttttca aattattata tttccacatg aaaagcccat ttatccgaag gtcataagat   7020
tattccctga caaaaaaaat ctaaaattat tcaaaataaa gaccaaaaac aaatattcaa   7080
aagaaagaga aaaaccccaa aagcataaac tttatcatac atgcacaaaa gaaaaaactt   7140
cgtatttgtt attcaaaaat gttctgtaaa tattaaatat cattctatat gtatttgtgt   7200
atttatatgt ttcacgcatt tttaacaaaa taagtcactg gaatagtcaa ttattttta   7260
gcaaaataat gatttttttt gtgtgtgtat tgttagctag gagttgtagg actaagatca   7320
tgattggcta ttattagatc caaatttatg ataagtgcaa caaactattt ttgttgatgg   7380
catagtgtgt gcaaagaaaa aaatcagaag agcaatgggg caaacagaga ggcgcaacat   7440
tatcccctag tccaagtaac caaagttctg ttcttgtgga gactgaattg ttcattggac   7500
ttcctgaatg gcgctaggcg ctaactacat taccctaaac tgtttagcgg cgcccaatct   7560
agtcgtgggt gactaactgc cgccaagccg ttttgtggcg gttcaaaccg ctacgaaatt   7620
ctctcagaac cgctgcaatc tgccggtttt catgtagtgc tagtgcaaca tattatatta   7680
attcactagt attgtactat cattttggaa gaaaagaaga tcatcctcaa taatgtgtca   7740
tatatcatgc tttcatttcc tagtgatgaa gaaaaaatgt agtatatata tatatatata   7800
tgccgcgttt attatttgct aaaatttttc attgttgtta cctaggtctg ttttgattcc   7860
ctccctattc ttgttgtaag ttttaagtaa ccaaggacag acataataat ttgatattct   7920
attacattct attacattct attacattat gtgtgtgttg tatcgtatta tatttgatat   7980
tctatttatc attatattct attgtgtgtg ttgttgtaag ttttaagtaa ccaaggacag   8040
acataataat ttgattcaag gtgtgttgta tccttatcat tatattcaat tctattta     8098
```

<210> SEQ ID NO 5
<211> LENGTH: 1267
<212> TYPE: DNA
<213> ORGANISM: Artificial Sequence
<220> FEATURE:
<223> OTHER INFORMATION: cDNA sequence of LBA5b.1 from Tifrunner

<400> SEQUENCE: 5

```
attgaggaaa taaaagtgtg tgagggccaa ataataagta gctacctgct gattattaat     60
taaatccatg tcaatctgct gcaactttga atctatccct ctctctaggg ttcctgatta    120
gtgctatttt catttcctaa ttgagctatt tataaagaag aagatggtga gaggaaagat    180
tgagatgaaa aggatagaga atgcaacaag ccgtcaagta acgttttcaa agaggaggag    240
tgggcttcta aagaaagcac atgagctttc tgttctttgt gatgcacaaa ttgctcttat    300
aatcttttca caaagtggga ggctctttga atactcaagt acttcagaca tggaacaaat    360
gttggaacgc taccgtcaat atgtagcaga tgatggtcgt atcaataata ttggagaatt    420
ccagcaattg gaatttgatc ccccaagctt ggctaagaag attgaacttc ttgagctttc    480
tcaaaggaag ctaatgggac agggcctgag ctcttgttca tttgatgaac tcgttggaat    540
tgagaatcag cttgtgtcaa gcttgcaaaa cattaggctc aaaaaggctc agctttatag    600
agagcatatt gaacaactac aaaataagga gaaggatttg ctcctagaga atgccaaatt    660
aactgaaatg tgtgtgcaaa gaaaaaaatc agaagagcga tgggacaaac agagagacac    720
aacattatcc cctagtccaa gtaaccaaag ttctgttctt gtggagactg aattgttcat    780
```

```
tggacttccc gaatggcgct aggcgctagt tacactaccc taaactgttt agcggcgccc    840

aatctagtcg cgggtgacta actgccgcca agccattttg tggcggttca aaccgctact    900

aaattctctc agaaccgctg caatctgccg gttttcgtgt agtgatgcaa catattatat    960

taactcacta gtattgtact atcattttgg aagaaaagaa gatcatcctc aataatgtgt   1020

cataaatcat gctttcattt cctagtgatg aagaaaaaat gtagtatata tatatatatg   1080

ccgcgtttat tatttgctaa aatttttcat tgttactacc taggtctgtt ttgatttcct   1140

ccctattttt gttgtaagtt ttaagtaacc aaggacagac ataataaaaa caaggtgtgt   1200

tgtatcgtat tattgtatgt acctatgtat gcttacatga tgattatatt atttgtcacg   1260

tccatta                                                             1267
```

<210> SEQ ID NO 6
<211> LENGTH: 2134
<212> TYPE: DNA
<213> ORGANISM: Artificial Sequence
<220> FEATURE:
<223> OTHER INFORMATION: cDNA sequence of LBA5b.2 from Tifrunner

<400> SEQUENCE: 6

```
tatctttttt ttttttctg ggctgttcat catatttttt gtacagtgtt tgatattttt      60

ccctgggtta atgtctccat aatctcattt tggagcttgt gggtaccact gtttttgata    120

aaaatagaat ctttacttct gttttatctg gattgtgggt tctcactgtc catccattcc    180

attgcaaatt caagcatata tatgtttcca gcttcatatc tagctagcta tagctgctag    240

gaatataaat aaaaacccta gctttctttc tctgattctt gtgaaagaaa gagagagcac    300

aagggaacct ttctgagaag ctttaataat ttccaacaat tgcataagaa gaagatggtg    360

agaggaaaga ttgagatgaa aaggatagag aatgcaacaa gccgtcaagt aacgttttca    420

aagaggagga gtgggcttct aaagaaagca catgagcttt ctgttctttg tgatgcacaa    480

attgctctta taatcttttc acaaagtggg aggctctttg aatactcaag tacttcagac    540

atggaacaaa tgttggaacg ctaccgtcaa tatgtagcag atgatggtcg tatcaataat    600

attggagaat tccagcaatt ggaatttgat cccccaagct tggctaagaa gattgaactt    660

cttgagcttt ctcaaaggaa gctaatggga cagggcctga gctcttgttc atttgatgaa    720

ctcgttggaa ttgagaatca gcttgtgtca agcttgcaaa acattaggct caaaaaggct    780

cagctttata gagagcatat tgaacaacta caaaataagg agaaggattt gctcctagag    840

aatgccaaat taactgaaat gtgtgtgcaa agaaaaaaat cagaagagcg atgggacaaa    900

cagagagaca caacattatc ccctagtcca agtaaccaaa gttctgttct tgtggagact    960

gaattgttca ttggacttcc cgaatggcgc taggcgctag ttacactacc ctaaactgtt   1020

tagcggcgcc caatctagtc gcgggtgact aactgccgcc aagccatttt gtggcggttc   1080

aaaccgctac taaattctct cagaaccgct gcaatctgcc ggttttcgtg tagtgatgca   1140

acatattata ttaactcact agtattgtac tatcattttg gaagaaaaga agatcatcct   1200

caataatgtg tcataaatca tgctttcatt tcctagtgat gaagaaaaaa tgtagtatat   1260

atatatatat gccgcgttta ttatttgcta aaatttttca ttgttactac ctaggtctgt   1320

tttgatttcc tccctatttt tgttgtaagt tttaagtaac caaggacaga cataataaaa   1380

acaaggtgtg ttgtatcgta ttattgtatg tacctatgta tgcttacatg atgattatat   1440

tatttgtcac gtccattagg ttttcgtgta gtgatgcaac atattatatt aactcactag   1500

tattgtacta tcattttgga agaaaagaag atcatcctca ataatgtgtc ataaatcatg   1560
```

```
ctttcatttc ctagtgatga agaaaaaatg tagtatatat atatatatgc cgcgtttatt   1620

atttgctaaa atttttcatt gttactacct aggtctgttt tgatttcctc cctatttttg   1680

ttgtaagttt taagtaacca aggacagaca taataaaaac aaggtgtgtt gtatcgtatt   1740

attgtatgta cctatgtatg cttacatgat gattatatta tttgtcacgt ccattaggtt   1800

ttcgtgtagt gatgcaacat attatattaa ctcactagta ttgtactatc attttggaag   1860

aaaagaagat catcctcaat aatgtgtcat aaatcatgct ttcatttcct agtgatgaag   1920

aaaaaatgta gtatatatat atatatgccg cgtttattat ttgctaaaat ttttcattgt   1980

tactacctag gtctgttttg atttcctccc tatttttgtt gtaagtttta agtaaccaag   2040

gacagacata ataaaaacaa ggtgtgttgt atcgtattat tgtatgtacc tatgtatgct   2100

tacatgatga ttatattatt tgtcacgtcc atta                              2134
```

```
<210> SEQ ID NO 7
<211> LENGTH: 1404
<212> TYPE: DNA
<213> ORGANISM: Artificial Sequence
<220> FEATURE:
<223> OTHER INFORMATION: cDNA sequence of LBA5b.3 from Tifrunner

<400> SEQUENCE: 7
```

```
attgaggaaa taaaagtgtg tgagggccaa ataataagta gctacctgct gattattaat     60

taaatccatg tcaatctgct gcaactttga atctatccct ctctctaggg ttcctgatta    120

gtgctatttt catttcctaa ttgagctatt tataaagaag aagatggtga gaggaaagat    180

tgagatgaaa aggatagaga atgcaacaag ccgtcaagta acgttttcaa agaggaggag    240

tgggcttcta aagaaagcac atgagctttc tgttctttgt gatgcacaaa ttgctcttat    300

aatcttttca caaagtggga ggctctttga atactcaagt acttcagaca tggaacaaat    360

gttggaacgc taccgtcaat atgtagcaga tgatggtcgt atcaataata ttggagaatt    420

ccagcaattg gaatttgatc ccccaagctt ggctaagaag attgaacttc ttgagctttc    480

tcaaaggaag ctaatgggac agggcctgag ctcttgttca tttgatgaac tcgttggaat    540

tgagaatcag cttgtgtcaa gcttgcaaaa cattaggctc aaaaaggctc agctttatag    600

agagcatatt gaacaactac aaaataagga gaaggatttg ctcctagaga atgccaaatt    660

aactgaaatg gggtggcaat cgaggaagtc cgctccgtca aaagcccgcc atctgtgtgt    720

gcaaagaaaa aaatcagaag agcgatggga caaacagaga gacacaacat tatcccctag    780

tccaagtaac caaagttctg ttcttgtgga gactgaattg ttcattggac ttcccgaatg    840

gcgctaggcg ctagttacac taccctaaac tgtttagcgg cgcccaatct agtcgcgggt    900

gactaactgc cgccaagcca ttttgtggcg gttcaaaccg ctactaaatt ctctcagaac    960

cgctgcaatc tgccggtttt cgtgtagtga tgcaacatat tatattaact cactagtatt   1020

gtactatcat tttggaagaa aagaagatca tcctcaataa tgtgtcataa atcatgcttt   1080

catttcctag tgatgaagaa aaaatgtagt atatatatat atatgccgcg tttattattt   1140

gctaaaattt ttcattgtta ctacctaggt ctgttttgat ttcctcccta tttttgttgt   1200

aagttttaag taaccaagga cagacataat aaaaacaagg tgtgttgtat cgtattattg   1260

tatgtaccta tgtatgctta catgatgatt atattatttg tcacgtccat tacctatgta   1320

tgcttacatg atgattatat tatttgtcac gtccattacc tatgtatgct tacatgatga   1380

ttatattatt tgtcacgtcc atta                                         1404
```

<210> SEQ ID NO 8
<211> LENGTH: 2359
<212> TYPE: DNA
<213> ORGANISM: Artificial Sequence
<220> FEATURE:
<223> OTHER INFORMATION: cDNA sequence of LBA5b.4 from Tifrunner

<400> SEQUENCE: 8

```
tatctttttt tttttttctg ggctgttcat catatttttt gtacagtgtt tgatattttt     60
ccctgggtta atgtctccat aatctcattt tggagcttgt gggtaccact gtttttgata    120
aaaatagaat ctttacttct gttttatctg gattgtgggt tctcactgtc catccattcc    180
attgcaaatt caagcatata tatgtttcca gcttcatatc tagctagcta tagctgctag    240
gaatataaat aaaaaaccta gctttctttc tctgattctt gtgaaagaaa gagagagcac    300
aagggaacct ttctgagaag ctttaataat ttccaacaat tgcataagaa gaagatggtg    360
agaggaaaga ttgagatgaa aaggatagag aatgcaacaa gccgtcaagt aacgttttca    420
aagaggagga gtgggcttct aaagaaagca catgagcttt ctgttctttg tgatgcacaa    480
attgctctta taatcttttc acaaagtggg aggctctttg aatactcaag tacttcagac    540
atggaacaaa tgttggaacg ctaccgtcaa tatgtagcag atgatggtcg tatcaataat    600
attggagaat tccagcaatt ggaatttgat cccccaagct tggctaagaa gattgaactt    660
cttgagcttt ctcaaaggaa gctaatggga cagggcctga gctcttgttc atttgatgaa    720
ctcgttggaa ttgagaatca gcttgtgtca agcttgcaaa acattaggct caaaaaggct    780
cagctttata gagagcatat tgaacaacta caaaataagg agaaggattt gctcctagag    840
aatgccaaat taactgaaat ggggtggcaa tcgaggaagt ccgctccgtc aaaagcccgc    900
catctgtgtg tgcaaagaaa aaaatcagaa gagcgatggg acaaacagag agacacaaca    960
ttatccccta gtccaagtaa ccaaagttct gttcttgtgg agactgaatt gttcattgga   1020
cttcccgaat ggcgctaggc gctagttaca ctaccctaaa ctgtttagcg gcgcccaatc   1080
tagtcgcggg tgactaactg ccgccaagcc attttgtggc ggttcaaacc gctactaaat   1140
tctctcagaa ccgctgcaat ctgccggttt tcgtgtagtg atgcaacata ttatattaac   1200
tcactagtat tgtactatca ttttggaaga aaagaagatc atcctcaata atgtgtcata   1260
aatcatgctt tcatttccta gtgatgaaga aaaaatgtag tatatatata tatatgccgc   1320
gtttattatt tgctaaaatt tttcattgtt actacctagg tctgttttga tttcctccct   1380
atttttgttg taagttttaa gtaaccaagg acagacataa taaaaacaag gtgtgttgta   1440
tcgtattatt gtatgtacct atgtatgctt acatgatgat tatattattt gtcacgtcca   1500
ttacaatcta gtcgcgggtg actaactgcc gccaagccat tttgtggcgg ttcaaaccgc   1560
tactaaattc tctcagaacc gctgcaatct gccggttttc gtgtagtgat gcaacatatt   1620
atattaactc actagtattg tactatcatt ttggaagaaa agaagatcat cctcaataat   1680
gtgtcataaa tcatgctttc atttcctagt gatgaagaaa aaatgtagta tatatatata   1740
tatgccgcgt ttattatttg ctaaaatttt tcattgttac tacctaggtc tgttttgatt   1800
tcctccctat ttttgttgta agttttaagt aaccaaggac agacataata aaaacaaggt   1860
gtgttgtatc gtattattgt atgtacctat gtatgcttac atgatgatta tattatttgt   1920
cacgtccatt acaatctagt cgcgggtgac taactgccgc caagccattt tgtggcggtt   1980
caaaccgcta ctaaattctc tcagaaccgc tgcaatctgc cggttttcgt gtagtgatgc   2040
aacatattat attaactcac tagtattgta ctatcatttt ggaagaaaag aagatcatcc   2100
```

```
tcaataatgt gtcataaatc atgctttcat ttcctagtga tgaagaaaaa atgtagtata   2160

tatatatata tgccgcgttt attatttgct aaaatttttc attgttacta cctaggtctg   2220

ttttgatttc ctccctattt ttgttgtaag ttttaagtaa ccaaggacag acataataaa   2280

aacaaggtgt gttgtatcgt attattgtat gtacctatgt atgcttacat gatgattata   2340

ttatttgtca cgtccatta                                                2359
```

```
<210> SEQ ID NO 9
<211> LENGTH: 1182
<212> TYPE: DNA
<213> ORGANISM: Artificial Sequence
<220> FEATURE:
<223> OTHER INFORMATION: cDNA sequence of LBA5a.1 from A. duranensis

<400> SEQUENCE: 9

tttctttttc tttttctttt tctttttga ataaatgaac aacctacaac ctagctagct     60

tcttagttac tttttgaata atttaattaa ttaattaatt ttttttgttt tgtgggggtt    120

tgtagaagaa gaagatggtg agaggaaaga ttgagatgaa acggatagag aatgcaacaa    180

gccgtcaagt aacgttttca aagaggagga gtgggcttct aaagaaagca catgagcttt    240

ctgttctttg tgatgcacaa attgctctta taatcttttc acaaagtggg aggctctttg    300

aatactcaag tacttcagac atggatcaac ttttggaacg ctaccgtcaa tatgtagcag    360

atgatggtcg tatcaataat attggagaat tccagcaatt ggaatttgat cccccaagct    420

tggctaagaa gattgaactt cttgagcttt ctcaaaggaa gctaatggga cagggcctga    480

gctcttgttc atttgatgaa ctcgttggaa ttgagaatca gcttgtgtca agcttgcaaa    540

acattaggct caaaaaggct cagctttata gagagcatat tgaacaacta caaaataagg    600

agaaggattt gctcctggag aatgccaaat taactgaaat gtgtgtgcaa agaaaaaaat    660

cagaagagca atggggcaaa cagagaggcg caacattatc ccctagtcca agtaaccaaa    720

gttctgttct tgtggagact gaattgttca ttggacttcc tgaatggcgc taggcgctaa    780

ctacattacc ctaaactgtt tagcggcgcc caatctagtc gtgggtgact aactgccgcc    840

aagccgtttt gtggcggttc aaaccgctac gaaattctct cagaaccgct gcaatctgcc    900

ggttttcatg tagtgctagt gcaacatatt atattaattc actagtattg tactatcatt    960

ttggaagaaa agaagatcat cctcaataat gtgtcatata tcatgctttc atttcctagt   1020

gatgaagaaa aaatgtagta tatatatata tatatatgcc gcgtttatta tttgctaaaa   1080

tttttcattg ttgttaccta ggtctgtttt gattccctcc ctattcttgt tgtaagtttt   1140

aagtaaccaa ggacagacat aataaaaaca aggtgtgttg ta                      1182
```

```
<210> SEQ ID NO 10
<211> LENGTH: 1266
<212> TYPE: DNA
<213> ORGANISM: Artificial Sequence
<220> FEATURE:
<223> OTHER INFORMATION: cDNA sequence of LBA5a.2 from A. duranensis

<400> SEQUENCE: 10

tttctttttc tttttctttt tctttttga ataaatgaac aacctacaac ctagctagct     60

tcttagttac tttttgaata atttaattaa ttaattaatt ttttttgttt tgtgggggtt    120

tgtagaagaa gaagatggtg agaggaaaga ttgagatgaa acggatagag aatgcaacaa    180

gccgtcaagt aacgttttca aagaggagga gtgggcttct aaagaaagca catgagcttt    240
```

```
ctgttctttg tgatgcacaa attgctctta taatcttttc acaaagtggg aggctctttg    300

aatactcaag tacttcagac atggatcaac ttttggaacg ctaccgtcaa tatgtagcag    360

atgatggtcg tatcaataat attggagaat tccagcaatt ggaatttgat cccccaagct    420

tggctaagaa gattgaactt cttgagcttt ctcaaaggaa gctaatggga cagggcctga    480

gctcttgttc atttgatgaa ctcgttggaa ttgagaatca gcttgtgtca agcttgcaaa    540

acattaggct caaaaaggtc attaataatt tacaacatta tattatatta tatataaata    600

taagaacaag acgttcttga tataatttaa tgtattttca ggctcagctt tatagagagc    660

atattgaaca actacaaaat aaggagaagg atttgctcct ggagaatgcc aaattaactg    720

aaatgtgtgt gcaaagaaaa aaatcagaag agcaatgggg caaacagaga ggcgcaacat    780

tatcccctag tccaagtaac caaagttctg ttcttgtgga gactgaattg ttcattggac    840

ttcctgaatg gcgctaggcg ctaactacat taccctaaac tgtttagcgg cgcccaatct    900

agtcgtgggt gactaactgc cgccaagccg ttttgtggcg gttcaaaccg ctacgaaatt    960

ctctcagaac cgctgcaatc tgccggtttt catgtagtgc tagtgcaaca tattatatta   1020

attcactagt attgtactat cattttggaa gaaaagaaga tcatcctcaa taatgtgtca   1080

tatatcatgc tttcatttcc tagtgatgaa gaaaaaatgt agtatatata tatatatata   1140

tgccgcgttt attatttgct aaaatttttc attgttgtta cctaggtctg ttttgattcc   1200

ctccctattc ttgttgtaag ttttaagtaa ccaaggacag acataataaa aacaaggtgt   1260

gttgta                                                               1266
```

```
<210> SEQ ID NO 11
<211> LENGTH: 230
<212> TYPE: PRT
<213> ORGANISM: Artificial Sequence
<220> FEATURE:
<223> OTHER INFORMATION: Amino acid sequence of LBA5b.1 from Tifrunner

<400> SEQUENCE: 11

Met Gly Ala Ser Thr Asn Phe Trp Tyr Asp Thr Lys Ser Val Ile Glu
1               5                   10                  15

Glu Ile Lys Lys Lys Lys Met Val Arg Gly Lys Ile Glu Met Lys Arg
            20                  25                  30

Ile Glu Asn Ala Thr Ser Arg Gln Val Thr Phe Ser Lys Arg Arg Ser
        35                  40                  45

Gly Leu Leu Lys Lys Ala His Glu Leu Ser Val Leu Cys Asp Ala Gln
    50                  55                  60

Ile Ala Leu Ile Ile Phe Ser Gln Ser Gly Arg Leu Phe Glu Tyr Ser
65                  70                  75                  80

Ser Thr Ser Asp Met Glu Gln Met Leu Glu Arg Tyr Arg Gln Tyr Val
                85                  90                  95

Ala Asp Asp Gly Arg Ile Asn Asn Ile Gly Glu Phe Gln Gln Leu Glu
            100                 105                 110

Phe Asp Pro Pro Ser Leu Ala Lys Lys Ile Glu Leu Leu Glu Leu Ser
        115                 120                 125

Gln Arg Lys Leu Met Gly Gln Gly Leu Ser Ser Cys Ser Phe Asp Glu
    130                 135                 140

Leu Val Gly Ile Glu Asn Gln Leu Val Ser Ser Leu Gln Asn Ile Arg
145                 150                 155                 160

Leu Lys Lys Val Leu Lys Lys Val Glu Leu Glu Asn Ser Pro Glu Arg
                165                 170                 175
```

```
Gln Arg Lys Val Leu Lys Val Glu Leu Glu Asn Ser Pro Glu Arg Gln
            180                 185                 190

Arg Lys Val Glu Leu Lys Val Leu Ser Asn Pro Glu Ser Leu Gln Gly
        195                 200                 205

Leu Ser Ser Cys Ser Phe Asp Glu Leu Val Gly Ile Glu Asn Gln Leu
    210                 215                 220

Val Ser Ser Leu Gln Asn
225                 230


<210> SEQ ID NO 12
<211> LENGTH: 246
<212> TYPE: PRT
<213> ORGANISM: Artificial Sequence
<220> FEATURE:
<223> OTHER INFORMATION: Amino acid sequence of LBA5b.2 from Tifrunner

<400> SEQUENCE: 12

Met Val Arg Gly Lys Ile Glu Met Lys Arg Ile Glu Asn Ala Thr Ser
1               5                   10                  15

Arg Gln Val Thr Phe Ser Lys Arg Arg Ser Gly Leu Leu Lys Lys Ala
            20                  25                  30

His Glu Leu Ser Val Leu Cys Asp Ala Gln Ile Ala Leu Ile Ile Phe
        35                  40                  45

Ser Gln Ser Gly Arg Leu Phe Glu Tyr Ser Ser Thr Ser Asp Met Glu
    50                  55                  60

Gln Met Leu Glu Arg Tyr Arg Gln Tyr Val Ala Asp Asp Gly Arg Ile
65                  70                  75                  80

Asn Asn Ile Gly Glu Phe Gln Gln Leu Glu Phe Asp Pro Pro Ser Leu
                85                  90                  95

Ala Lys Lys Ile Glu Leu Leu Glu Leu Ser Gln Arg Lys Leu Met Gly
            100                 105                 110

Gln Gly Leu Ser Ser Cys Ser Phe Asp Glu Leu Val Gly Ile Glu Asn
        115                 120                 125

Gln Leu Val Ser Ser Leu Gln Asn Ile Arg Leu Lys Lys Ala Gln Leu
    130                 135                 140

Tyr Arg Glu His Ile Glu Gln Leu Gln Asn Lys Glu Lys Val Leu Lys
145                 150                 155                 160

Lys Val Leu Val Glu Ser Leu Val Glu Ser Leu Val Glu Ser Leu Val
                165                 170                 175

Glu Ser Leu Val Glu Ser Leu Gln Ser Leu Val Glu Ser Leu Gln Ser
            180                 185                 190

Leu Val Glu Ser Leu Gln Ser Arg Gln Ser Leu Val Glu Ser Leu Gln
        195                 200                 205

Ser Leu Val Glu Ser Leu Gln Ser Arg Gln Leu Val Glu Ser Leu Gln
    210                 215                 220

Leu Val Glu Ser Leu Gln Ser Leu Pro Glu His Leu Gln Leu Arg Gln
225                 230                 235                 240

Leu Val Glu Ser Lys Leu
                245


<210> SEQ ID NO 13
<211> LENGTH: 243
<212> TYPE: PRT
<213> ORGANISM: Artificial Sequence
<220> FEATURE:
<223> OTHER INFORMATION: Amino acid sequence encoded by LBA5a.1 from A.
      duranensis
```

<400> SEQUENCE: 13

Met Val Arg Gly Lys Ile Glu Met Lys Arg Ile Glu Asn Ala Thr Ser
1               5                   10                  15

Arg Gln Val Thr Phe Ser Lys Arg Arg Ser Gly Leu Leu Lys Lys Ala
            20                  25                  30

His Glu Leu Ser Val Leu Cys Asp Ala Gln Ile Ala Leu Ile Ile Phe
        35                  40                  45

Ser Gln Ser Gly Arg Leu Phe Glu Tyr Ser Ser Thr Ser Asp Met Asp
    50                  55                  60

Gln Leu Leu Glu Arg Tyr Arg Gln Tyr Val Ala Asp Asp Gly Arg Ile
65                  70                  75                  80

Asn Asn Ile Gly Glu Phe Gln Gln Leu Glu Phe Asp Pro Pro Ser Leu
                85                  90                  95

Ala Lys Lys Ile Glu Leu Leu Glu Leu Ser Gln Arg Lys Leu Met Gly
            100                 105                 110

Gln Gly Leu Ser Ser Cys Ser Phe Asp Glu Leu Val Gly Ile Glu Asn
        115                 120                 125

Gln Leu Val Ser Ser Leu Gln Asn Ile Arg Leu Lys Lys Ala Gln Leu
    130                 135                 140

Tyr Arg Glu His Ile Glu Gln Leu Gln Asn Lys Glu Lys Asp Leu Leu
145                 150                 155                 160

Lys Lys Ala Gln Leu Tyr Arg Glu His Ile Glu Gln Leu Gln Asn Lys
                165                 170                 175

Glu Lys Asp Leu Leu Lys Lys Ala Gln Leu Tyr Arg Glu His Ile Glu
            180                 185                 190

Gln Leu Gln Asn Lys Glu Lys Val Leu Lys Lys Val Leu Lys Lys Val
        195                 200                 205

Leu Val Glu Thr Glu Leu Pro Ser Asn Pro Glu Thr Leu Ser Lys Val
    210                 215                 220

Leu Lys Lys Val Leu Val Glu Gln Leu Tyr Arg Glu His Ile Glu Gln
225                 230                 235                 240

Leu Lys Glu

<210> SEQ ID NO 14
<211> LENGTH: 161
<212> TYPE: PRT
<213> ORGANISM: Artificial Sequence
<220> FEATURE:
<223> OTHER INFORMATION: Amino acid sequence encoded by LBA5a.2 from A. duranensis

<400> SEQUENCE: 14

Met Val Arg Gly Lys Ile Glu Met Lys Arg Ile Glu Asn Ala Thr Ser
1               5                   10                  15

Arg Gln Val Thr Phe Ser Lys Arg Arg Ser Gly Leu Leu Lys Lys Ala
            20                  25                  30

His Glu Leu Ser Val Leu Cys Asp Ala Gln Ile Ala Leu Ile Ile Phe
        35                  40                  45

Ser Gln Ser Gly Arg Leu Phe Glu Tyr Ser Ser Thr Ser Asp Met Asp
    50                  55                  60

Gln Leu Leu Glu Arg Tyr Arg Gln Tyr Val Ala Asp Asp Gly Arg Ile
65                  70                  75                  80

Asn Asn Ile Gly Glu Phe Gln Gln Leu Glu Phe Asp Pro Pro Ser Leu
                85                  90                  95

Ala Lys Lys Ile Glu Leu Leu Glu Leu Ser Gln Arg Lys Leu Met Gly

```
        100                 105                 110

Gln Gly Leu Ser Ser Cys Ser Phe Asp Glu Leu Val Gly Ile Glu Asn
        115                 120                 125

Gln Leu Val Ser Ser Leu Gln Asn Ile Arg Leu Lys Lys Val Ile Asn
    130                 135                 140

Asn Leu Gln His Tyr Ile Ile Leu Tyr Ile Asn Ile Arg Thr Arg Arg
145                 150                 155                 160

Ser


<210> SEQ ID NO 15
<211> LENGTH: 1985
<212> TYPE: DNA
<213> ORGANISM: Arachis hypogaea L. variety Tifrunner
<220> FEATURE:
<221> NAME/KEY: promoter
<222> LOCATION: (1)..(1985)
<223> OTHER INFORMATION: Promoter sequence of LBA5b from Tifrunner

<400> SEQUENCE: 15

attagatgta tggattttct tattattaat tagtaaacta gatatataac tctttattta     60

tttttctcta atagttaaga tttttatgat aaatagacta atcatattat gtgtatacta    120

ttatactaaa gttattaaat taaacataat ataaaatata tattgaaaaa taaaatatat    180

attaaaaata aaataaataa tacatatatt tatatataaa tatataataa ttaatttaat    240

aattaatttt tagtgtatac aataatattt ttatttaccg acatagtgct aatagagttt    300

ttatcattaa acattatttt agaattcaat ttttgttata caacaaaaat ttttagcaaa    360

aaacaaacaa aaatagatga aaagactcaa aaataagttt accttttaag tttaggaaaa    420

atttttgggt gaacgatatg ttagagatat tatcattcat atatatctat ctagcagtat    480

aaaattttaa atttttagac taaataattt cacgacaatt aaaaagttaa agtcttttaa    540

gtttttaaaa tatgtatttt aaaaacattt taaaacttcc aaaacagata atcttaataa    600

ttgttatcaa gagattatgt aatattaata ttaacaaaat aataacataa tttaccttta    660

attaataccg taaacttatg aatccgtcct ctgataaata tggttgttaa ttacccttaa    720

aaataacgcg tcaacgaaac cattatttta tcttcaggtc taattaaggc tataattaca    780

agagttgtcc gatccaacaa aaaaaaaaaa tgctaaagag agagagagag agcgagatta    840

tgtttatttt cattatatta ctttttaaaa atttaagtag atagggagaa acatgaaaat    900

aaacttttaa atcatactga tatcataata taattctttt atttatttta tattattttt    960

tatataataa aaataaagta taaactttta aatcatacaa attctgatat catattatat   1020

tattttttct taaacactta cactgattaa aaaagaaaga tctctatcaa atttgatccc   1080

tctaataata atggagtgag ttttggcttt ctgtgctttg aattacagaa gcttgtatat   1140

tttgtgccct accttttctt gtttttacca aatgggggca tccaccaact tctggtatga   1200

taccaaaagt gtgattgagg aaataaaagt gtgtgagggc caaataataa gtagctacct   1260

gctgattatt aattaaatcc atgtcaatct gctgcaactt tgaatctatc cctctctcta   1320

gggttcctga ttagtgctat tttcatttcc taattgagct atttatagta ataacatatt   1380

ccctctcaat aattcctctg ttctttgtac atatgaacag atactccatt ttaaagtgtg   1440

aagctttcca agtatctttt tttttttct gggctgttca tcatattttt tgtacagtgt   1500

ttgatatttt tccctgggtt aatgtctcca taatctcatt ttggagcttg tgggtaccac   1560

tgtttttgat aaaaatagaa tctttacttc tgttttatct ggattgtggg ttctcactgt   1620
```

```
ccatccattc cattgcaaat tcaagcatat atatgtttcc agcttcatat ctagctagct   1680

atagctgcta ggaatataaa taaaaaccct agctttcttt ctctgattct tgtgaaagaa   1740

agagagagag cacaagggaa cctttctgag aagctttaat aatttccaac aattgcatgt   1800

gtgttctctt tttccaacct ccttctacaa cctccatagt ttgtgcttga aagggatttt   1860

tctttttctt ttgtttttttc tttttgaat aaatgaacaa cctacctttt ttgatttttg   1920

atttttagat ttttagattg attattgagt ttattgagtt tattgaattt tgaattttga   1980

attta                                                               1985
```

```
<210> SEQ ID NO 16
<211> LENGTH: 2094
<212> TYPE: DNA
<213> ORGANISM: Arachis hypogaea L. variety Tifrunner
<220> FEATURE:
<221> NAME/KEY: promoter
<222> LOCATION: (1)..(2094)
<223> OTHER INFORMATION: Promoter sequence of LBA5a from Tifrunner

<400> SEQUENCE: 16

tgctttaatt ggattatatg atattagttc taggtatgga atcttttcga gctactctat     60

ttcatttaat tactcatgct tattcaaaaa cattgttatt cttaggatct ggatcaatta    120

ttcattcaat ggaaactatg gctagatatt ctccaaaaaa aaagttaaaa catggttatt    180

atggatggat taacaaaaca tacgttaatt ataaaaacag ctttttttaat aggtacgtgt    240

aatagagttt ttatcactaa atattatttt tagaatttaa tttttgtaat actacaaaaa    300

tttgtagcaa aaaacaaaca aaaatagatg aaaagactcg aaaacaagtt taccttcaag    360

atcaaaaatt ttttttgggt aaacgatatg ctaaagatat tatcattcat atgtatctat    420

ctaatggcat aaaatcttaa atttttacac taaataattt tacgacaatt aaaaagttaa    480

aagtctttta agtttttaaa agatgtattg taaaaacatt ttaaaacttc ccaaacggat    540

aatcttaata attgttatca aaagattatg taatattaat attaacaaaa taataacata    600

atttactttt aattaatacc gtaaacttat gaatccatcc tttgataaat atggctgtta    660

attacccttc aaaataacgc gtcaacgaaa ccattatttt atcttcaggt ctaattaagg    720

ctataattac aagagttgtc cgatccaaaa aagaaaaaaa aagctagaga gagagagcga    780

gattatgttt attttcatgt ttcagatttt tttttattat aattcatttt acattatatt    840

acttttaaaa aatttaagta gatagggaaa aacatattaa taattaacag ttgatcacat    900

tctctcggac aagaattttt ttggagattt acttgaaaat tttttataaa aatattttat    960

ttattttata ttattttttta tataataaaa ataaagtata aacttttaaa tcatacaaat   1020

tctgatatca tattatatta attttcttaa atacttacac tgattaaaaa aaaaatctat   1080

gggtctatca aatttcatcc ctctaataat aacaatggag gtttgaatta cagaaggttg   1140

tatattttgt gccctacctt ttcttgtttt taccaaatgg gggcatccac caacttctgg   1200

tatgatacca aaagtgtgaa tgaggaaata aaagtgtgtg agggccaaat aataagtagc   1260

tacctgctga ttatttatgg ctttatttat tataaatcca tgtctgctcc aactttgaat   1320

ctatctctct ctctagggtt cctgattagt gctattttca tttcctaatt gagctattta   1380

tagtaataac atattccctc tcaataattc ctctgttctt tgtacatatg aacagatact   1440

ccattttaaa gtgtgaagct ttccaagtat cttttttttc tgggctgttc atcatatttt   1500

tgtacagtgt ttgatatttt tccctgggtt aatgtctcca taatctcatt ttggagcttg   1560

tgggtaccac tgtttttgat aaaaatagaa tctttacttc tgtttttatc tggattgtgg   1620
```

gttctcactg tccattccat tgcaaattca agcatatatg tttccagctt catatctagc 1680
tagctatagc tgctaggaat ataaataaaa accctagctt tctttctccg atcctgtgtg 1740
aaagaaagag agagagagag cagaagggaa cctttctgag aagctttaat aatttccaac 1800
aattgcatgt gtgttctctt tttccaacct ccttctacaa cctccatagt ttgtgcttga 1860
aagggatttt tctttttctt tttttcttaa gagagagcag aagggaacct ttctgagaag 1920
ctttaataat ttccaacaat tgcatgtgtg ttctcttttt ccaacctcct tctacaacct 1980
ccatagtttg tgcttgaaag ggatttttct ttttcttttt ttcttaatta aattgattta 2040
gttgattagt tgattagtta gttgattagt tgattagatt gattagttga ttga 2094

<210> SEQ ID NO 17
<211> LENGTH: 20
<212> TYPE: DNA
<213> ORGANISM: Artificial Sequence
<220> FEATURE:
<223> OTHER INFORMATION: cloning primer sequence LBA5b-F

<400> SEQUENCE: 17
tttggctttc tgtgctttga 20

<210> SEQ ID NO 18
<211> LENGTH: 20
<212> TYPE: DNA
<213> ORGANISM: Artificial Sequence
<220> FEATURE:
<223> OTHER INFORMATION: cloning primer sequence LBA5b-R

<400> SEQUENCE: 18
tggcttggcg gcagttagtc 20

<210> SEQ ID NO 19
<211> LENGTH: 31
<212> TYPE: DNA
<213> ORGANISM: Artificial Sequence
<220> FEATURE:
<223> OTHER INFORMATION: overexpression vector primer LBA5b-OE-F
<220> FEATURE:
<221> NAME/KEY: misc_feature
<222> LOCATION: (1)..(6)
<223> OTHER INFORMATION: HindIII

<400> SEQUENCE: 19
aagcttatgg tgagaggaaa gattgagatg a 31

<210> SEQ ID NO 20
<211> LENGTH: 25
<212> TYPE: DNA
<213> ORGANISM: Artificial Sequence
<220> FEATURE:
<223> OTHER INFORMATION: overexpression vector primer LBA5b-OE-R
<220> FEATURE:
<221> NAME/KEY: misc_feature
<222> LOCATION: (1)..(6)
<223> OTHER INFORMATION: Pst1

<400> SEQUENCE: 20
ctgcagctag cgccattcgg gaagt 25

<210> SEQ ID NO 21
<211> LENGTH: 25
<212> TYPE: DNA
<213> ORGANISM: Artificial Sequence
<220> FEATURE:

<223> OTHER INFORMATION: sgRNA1 target sequence

<400> SEQUENCE: 21
tcgtgctgac cctgacactg tttga 25

<210> SEQ ID NO 22
<211> LENGTH: 25
<212> TYPE: DNA
<213> ORGANISM: Artificial Sequence
<220> FEATURE:
<223> OTHER INFORMATION: sgRNA2 target sequence

<400> SEQUENCE: 22
cttggcggta gccttgccga tttcc 25

<210> SEQ ID NO 23
<211> LENGTH: 25
<212> TYPE: DNA
<213> ORGANISM: Artificial Sequence
<220> FEATURE:
<223> OTHER INFORMATION: Cas9 detection primer CS4-F

<400> SEQUENCE: 23
tcgtgctgac cctgacactg tttga 25

<210> SEQ ID NO 24
<211> LENGTH: 25
<212> TYPE: DNA
<213> ORGANISM: Artificial Sequence
<220> FEATURE:
<223> OTHER INFORMATION: Cas9 detection primer CS4-R

<400> SEQUENCE: 24
cttggcggta gccttgccga tttcc 25

<210> SEQ ID NO 25
<211> LENGTH: 10648
<212> TYPE: DNA
<213> ORGANISM: Arachis hypogaea L. variety Luhua 11
<220> FEATURE:
<221> NAME/KEY: misc_feature
<222> LOCATION: (1)..(10648)
<223> OTHER INFORMATION: Genomic nucleotide sequence of LBA5a-2 from
Luhua 11

<400> SEQUENCE: 25
aagaagaaga tggtgagagg aaagattgag atgaaaagga tagagaatgc aacaagccgt 60
caagtaacgt tttcaaagag gaggagtggg cttctaaaga aagcacatga gctttctgtt 120
ctttgtgatg cacaaattgc tcttataatc ttttcacaaa gtgggaggct ctttgaatac 180
tcaagtactt cagagtaagc ccttacttaa tcactttatt ttcttgcttc atcaacattc 240
atgttagtgt tagtttcatt ctttaatttt tattcttctc ctaattaatt agtacaatac 300
tactacttat tattgaacta ttatatatat ggtttaatac aatgcgaatt aattagtaca 360
atacatttcc tatctcaata gatcttcaat taagaggcta tataatctaa atgttgcaat 420
gtagggtttg tagccttgaa gcacatgcat atttcattta tttgcttctc ttttattgta 480
ttatgttttc ttttgttaat tgaatgaagg aatttttgtt agatagtata tatgtactta 540
aatgcaaggc taaatattca tatttacttt agatgaatat aaaattaaat ctgatgaatt 600
tctccttgtt tttgtctgaa attcaactca tgtatagtca gactattttc tgtatgatag 660
gtgaacatat atatattttt aaaaaataat attatgtaca tacaaaaatt aatcaccaaa 720

-continued

```
ttagttatca tgtagttaga tatatttaaa catgttacat acattttcaa tgtgtattta    780

tgagtagttg atttgactat tgatttttag tgtgcattta gtgcagttat ttttcctcag    840

tgaattgatt ttcatttttt tgtaatttaa atgttatatt taagcattta atattaattt    900

ttgaaaataa aaaatgaacc cataagatgt gataaatcgc aaatcttgaa tgcaaaaggc    960

tagttttttt tttttttaa gccctaatta tcatagcaag taaacaggtt aatccaatag   1020

gtttatgtca tttagtgcat ggtgggtcaa tagatccctg tttttcaac tcatgatgta   1080

ataatactcc ttattttcac attttatgct ccaacttttg tatctcataa cattcatgta   1140

gaaaatatgg attaacctga acttggagat ttttttaaaa aaaaaatcat attaattaac   1200

tgtatatctt catcatagga atgcctgcaa agttttttgc tgacattaat gaataatata   1260

atgttctgat tgctttgttt tcaatagcta cctcttaaca gtatatgttt ttaatttctt   1320

tgaaatgttt cagcatggaa caaatgttgg aacgctaccg tcaatatgta gcagatgatg   1380

gtcgtatcaa taatattgga gaattccagg tatagtaaag agaatatcta taatggtata   1440

gttaagttac catttaccgc tacgatacca acagtatttc tgtcaacttc tgctaacttt   1500

tatttataac tgtgtttaat ggaagtgttt ttctggatgt gtctaataaa aatgtctttt   1560

ttatgactga gtctaataaa agtgttttta taaatgtatt ttttggatgt gtctttttat   1620

acatgtgctt aaaatataat aattaattat tgttggcaat aaattgacag ataacctatt   1680

ggtaccctat atttttcctt taccaatata tataatatat attgactata atacctttta   1740

gttcttttaa aatttcagga ttatttaata atatatagtt ttatttattt gtagtatgaa   1800

aacctatata tatttcatca agacaactat ttggagctag cagctagcta ctcctaataa   1860

gtaataagca tgcgatattg atattcatag cacatttaat ttgataagaa agtgaagatt   1920

attaataaca cacgaccaga tcaatatata atattcatgt catgccatgc tattaatttt   1980

ttgggattat taaagatata actatttatg taattttttc gtcaatttaa gtttttagaa   2040

aaagtagttt cattagatgg tataagagtt tattggcatc tagagtaaat aaatttatta   2100

atgtggctgt tttattatta tacttcctcc ttcttaaatt atctgattct tttttatttt   2160

tttatttttg ttacattttt agttttaaga agttattaat taatttgttt cactataaat   2220

taaaaaagtt agaagaatag aattatgaat ggaaagagaa attaatatta agaacatttt   2280

tctttttttt tgtttgttct ttacattttt ttataaaatt taatgattat tttagtaatt   2340

atataattaa aaagagacag ataggtaaga gtaacgtttt atatatagta aaaattaaat   2400

tataatggat tgtaataaaa ttggttttat gctttgacat gcagcaattg gaatttgatc   2460

ccccaagctt ggctaagaag attgaacttc ttgagctttc tcaaaggtca atcctgtgtt   2520

taaatactaa tccgtttatt gctgttgttc atattctaat actgagtatt atattcatta   2580

atatttggtg tgccatgaaa ttttaattca ttgtttgaat ttgttaggaa gctaatggga   2640

cagggcctga gctcttgttc atttgatgaa ctcgttggaa ttgagaatca gcttgtgtca   2700

agcttgcaaa acattaggct caaaaaggtc attaataatt cacaacatta tattatatta   2760

tatagatgta tatatatata agaacaagac gttcttaatt taattaattt aatgtacttt   2820

caggctcagc tttatagaga gcatattgaa caactacaaa ataaggtacc tgagcttagt   2880

ttggatgcaa attatacatc tttaaagaat taaaaaaaat tgtataaatt attttaatta   2940

ggtttcatgg tggacatctg acacattttt atgtattgaa tccaggagaa ggatttgctc   3000

ctagagaatg ccaaattaac tgaaatggtg agttaccatt ttcttttcat gatttatagc   3060

tggtttgaca aatttattta gaaagttatt tataatttta ttgtgtttgg taaataaaaa   3120
```

```
aataatgcga ttgtatttgt agttttaaaa agtttgaagt attttgaaac aaaaatatta   3180
tgtttacact aaaaattcgt tattaaataa gtttttatgt atttgtatat aaataaatat   3240
gtagtttaat ttatttttaa tgagtttagt agcttatttt tgtagatatt tagtatggtt   3300
gattttgaaa gcacttaaga aaatattttt taaagttagt ttgtgtttat taaaattaaa   3360
atgtataata tatatttata tattaataaa tatttaaatt tattcttata ttaaaaagta   3420
taatttttgt ctctaaaatt ttcaaaatat ctgtaacgta aaatttgttt caattttgtt   3480
tctaacattt taaatatatt tcaattatac ctttgagggt aggggtggca atcgaggaag   3540
tccgctccgt caaaagcccg ccatctggtg ggtctactaa atctcttttt ttttttttta   3600
tgaactatta aatattaaat aatatatata atttcataac tattttaata aatttataat   3660
ttctaaatct acaaacaata aagtcttcat aattataaat atataataaa cataattata   3720
aataaaattt tttgaaacaa aatataaaca ttgttcaaaa tatataatta aacatcttca   3780
aatttataat caatcaaata taaaacataa tccaaaatat aatttagaac atctttaatt   3840
atctacaacc tcttgtgttt gtaaaaaaat gtccttgacc aaaaagacgc ctggttcggt   3900
ggggaagccc gctccgtcct gtcaaaatcc acggattaag cgatgcgggt tagacagatt   3960
tttaggtttg acggttttaa attttcagtc gttcaacccg tctttttag tgggttatac    4020
ggactaatct gatgaatttt ggcccgtttg tcacctcttt ttgagggtta acactattaa   4080
tggagatgct attgtgacaa ttatgtgctg acatgtcact aaaacgtggt aaaactcagc   4140
tattaacatg tcagggtagt actgtcatgt tatttgttat ccaactaagg aatataattg   4200
aaatataaaa aaccaagttg agttggtcta gtggtgagct cattggtttg cttaaacaag   4260
tgttttaaat cccgccttgt gcatgcagca acctattggc cagtgacaaa cccttaaatg   4320
gagcttagta ctgaggcgga ttagtccttg gcctaccggg ttggaggata ccgtggccaa   4380
ggataccgtg gaaaaaaaaa agaaatataa aaagtaaaat taaaactaaa tgttaaaaga   4440
taaaatgtga acattgagga taaaaataga atttattact ctattatttt taaataaaaa   4500
atatattaat aatattctta aaatatatca ggtttattga gatttatttt aatacaataa   4560
tatttttact aaaaaattat gataagaact acatattctt cttacaaaat tataaaaaat   4620
attttaaaaa tgtatcattt ttaatacata aaaatagctt tgataccttt aaaaatttct   4680
ttagtaatac ttttaataat ttgctaacaa acatgtgatt atgacaacta attaagtatt   4740
atatagactt attagtaaat tatataaaaa tattttaaaa agtatccaag tgatttttat   4800
ataataaaag ttatattttt taaaatattt ttatataatt ttctaaaatt ttatagtatt   4860
tataaaaaga tttattttca ataaaagata ttattatatt aaaatgagtc tcaataaagg   4920
atattatcaa aaactttatt gaatagtata ttctattttt gtcttaaatg tttatattta   4980
ttattgatct ttggtttcaa tattactctt gatgatttgt ttaatcatat cctggacaat   5040
tttacattcc tacattgaga gggttgtttt cacacaactg tcaaggcagt atctctgtta   5100
atagtgttag tatttaaaaa tataattaaa aaatatttaa aatattagaa ataaaattaa   5160
aataaattaa acgtctagtg tattttttaa tttttttttt caaattttta gacaaaatat   5220
atattttatc cgttacttta ttgtgatcaa gtttcatttg ggttcaaaat tctctttcta   5280
tgtctattat agtcaattta aactatgaaa tttatttcat caaatgtatt tattgaaagt   5340
tatttatcgt ttgatttatc gaatatatgt attacagttt taagaagtta tttttcaaaa   5400
gagaattttg ataaactgcg ggaaaaaata aaacctttat ccgattttgt ttttggcgaa   5460
```

```
aaattaacgc ttttggttgg gcttgtgttc cattttcgtt ctaactaaag aaattcttta   5520
ctacattgta ggcccaagac ctaatcccaa taacgtagtg atattttttt caaattatta   5580
tatttccaca tgaaaagccc atttatccga aggtcataag aataactaaa gtatacccaa   5640
aaaaaaaaac ctaaaaatta ttccctgacc aaaaaaaaaa tctaaaatta ttctaaataa   5700
agaccaaaaa taaatattca aaagagagag aaaattaaag aattttacat tttcgcaatc   5760
acaaagaaaa aacccaaaag cgtaaacttt atcacacatg cacaaaagaa aaaacttcgt   5820
atttgttatt caaaaaatgt tctataaata ttaaatatca ttctatatgt atttgtgtat   5880
atatatatgt tgtttcacac atttttaaca aaataagtca ctggaatagt caattatttt   5940
ttagcaaaat aatgaaattt tttatgaata ctaaatatat atatttttaa atatgtaaca   6000
actgattttg tgtctattaa gcatggttat taactattag tttatatttt ttaggtaata   6060
aacttttttt gataaataat tagcaaacaa aataatagaa gcacaatggt taagggtttg   6120
aactattatt atcaaatttt tttgtgtata gtagtttatg tatttttagc taggagttgt   6180
aggactaaga tcatgattgg ctattattag atctaaattt atgataagtg caacaaacta   6240
tttttgttga tggcatagtg tgtgcaaaga aaaaaatcag aagagcgatg ggacaaacag   6300
agagacacaa cattatcccc tagtccaagt aaccaaagtt ctgttcttgt ggagactgaa   6360
ttgttcattg gacttcccga atggcgctag gcgctagtta cactacccta aactgtttag   6420
cggcgcccaa tctagtcgcg ggtgactaac tgccgccaag ccattttgtg gcggttcaaa   6480
ccgctactaa attctctcag aaccgctgca atctgccggt tttcgtgtag tgatgcaaca   6540
tattatatta actcactagt attgtactat cattttggaa gaaaagaaga tcatcctcaa   6600
taatgtgtca taaatcatgc tttcatttcc tagtgatgaa gaaaaaatgt agtatatata   6660
tatatatgcc gcgtttatta tttgctaaaa tttttcattg ttactaccta ggtctgtttt   6720
gatttcctcc ctatttttgt tgtaagtttt aagtaaccaa ggacagacat aataaaaaca   6780
aggtgtgttg tatcgtatta ttgtatgtac ctatgtatgc ttacatgaga taaataatta   6840
gcaaacaaaa taatagaagc acaatggtta agggtttgaa ctattattat caaatttttt   6900
tgtgtatagt agtttatgta tttttagcta ggagttgtag gactaagatc atgattggct   6960
attattagat ctaaatttat gataagtgca acaaactatt tttgttgatg gcatagtgtg   7020
tgcaaagaaa aaaatcagaa gagcgatggg acaaacagag agacacaaca ttatccccta   7080
gtccaagtaa ccaaagttct gttcttgtgg agactgaatt gttcattgga cttcccgaat   7140
ggcgctaggc gctagttaca ctaccctaaa ctgtttagcg gcgcccaatc tagtcgcggg   7200
tgactaactg ccgccaagcc attttgtggc ggttcaaacc gctactaaat tctctcagaa   7260
ccgctgcaat ctgccggttt tcgtgtagtg atgcaacata ttatattaac tcactagtat   7320
tgtactatca ttttggaaga aaagaagatc atcctcaata atgtgtcata aatcatgctt   7380
tcatttccta gtgatgaaga aaaaatgtag tatatatata tatatgccgc gtttattatt   7440
tgctaaaatt tttcattgtt actacctagg tctgttttga tttcctccct atttttgttg   7500
taagttttaa gtaaccaagg acagacataa taaaaacaag gtgtgttgta tcgtattatt   7560
gtatgtacct atgtatgctt acatgagata aataattagc aaacaaaata atagaagcac   7620
aatggttaag ggtttgaact attattatca aatttttttg tgtatagtag tttatgtatt   7680
tttagctagg agttgtagga ctaagatcat gattggctat tattagatct aaatttatga   7740
taagtgcaac aaactatttt tgttgatggc atagtgtgtg caaagaaaaa aatcagaaga   7800
gcgatgggac aaacagagag acacaacatt atcccctagt ccaagtaacc aaagttctgt   7860
```

```
tcttgtggag actgaattgt tcattggact tcccgaatgg cgctaggcgc tagttacact   7920
accctaaact gtttagcggc gcccaatcta gtcgcgggtg actaactgcc gccaagccat   7980
tttgtggcgg ttcaaaccgc tactaaattc tctcagaacc gctgcaatct gccggttttc   8040
gtgtagtgat gcaacatatt atattaactc actagtattg tactatcatt ttggaagaaa   8100
agaagatcat cctcaataat gtgtcataaa tcatgctttc atttcctagt gatgaagaaa   8160
aaatgtagta tatatatata tatgccgcgt ttattatttg ctaaaatttt tcattgttac   8220
tacctaggtc tgttttgatt tcctccctat ttttgttgta agttttaagt aaccaaggac   8280
agacataata aaaacaaggt gtgttgtatc gtattattgt atgtacctat gtatgcttac   8340
atgaggagtt gtaggactaa gatcatgatt ggctattatt agatctaaat ttatgataag   8400
tgcaacaaac tatttttgtt gatggcatag tgtgtgcaaa gaaaaaaatc agaagagcga   8460
tgggacaaac agagagacac aacattatcc cctagtccaa gtaaccaaag ttctgttctt   8520
gtggagactg aattgttcat tggacttccc gaatggcgct aggcgctagt tacactaccc   8580
taaactgttt agcggcgccc aatctagtcg cgggtgacta actgccgcca agccattttg   8640
tggcggttca aaccgctact aaattctctc agaaccgctg caatctgccg gttttcgtgt   8700
agtgatgcaa catattatat taactcacta gtattgtact atcattttgg aagaaaagaa   8760
gatcatcctc aataatgtgt cataaatcat gctttcattt cctagtgatg aagaaaaaat   8820
gtagtatata tatatatatg ccgcgtttat tatttgctaa aatttttcat tgttactacc   8880
taggtctgtt ttgatttcct ccctattttt gttgtaagtt ttaagtaacc aaggacagac   8940
ataataaaaa caaggtgtgt tgtatcgtat tattgtatgt acctatgtat gcttacatga   9000
ggagttgtag gactaagatc atgattggct attattagat ctaaatttat gataagtgca   9060
acaaactatt tttgttgatg gcatagtgtg tgcaaagaaa aaaatcagaa gagcgatggg   9120
acaaacagag agacacaaca ttatccccta gtccaagtaa ccaaagttct gttcttgtgg   9180
agactgaatt gttcattgga cttcccgaat ggcgctaggc gctagttaca ctaccctaaa   9240
ctgtttagcg gcgcccaatc tagtcgcggg tgactaactg ccgccaagcc attttgtggc   9300
ggttcaaacc gctactaaat tctctcagaa ccgctgcaat ctgccggttt tcgtgtagtg   9360
atgcaacata ttatattaac tcactagtat tgtactatca ttttggaaga aaagaagatc   9420
atcctcaata atgtgtcata aatcatgctt tcatttccta gtgatgaaga aaaaatgtag   9480
tatatatata tatatgccgc gtttattatt tgctaaaatt tttcattgtt actacctagg   9540
tctgttttga tttcctccct atttttgttg taagttttaa gtaaccaagg acagacataa   9600
taaaaacaag gtgtgttgta tcgtattatt gtatgtacct atgtatgctt acatgaccga   9660
atggcgctag gcgctagtta cactacccta aactgtttag cggcgcccaa tctagtcgcg   9720
ggtgactaac tgccgccaag ccattttgtg gcggttcaaa ccgctactaa attctctcag   9780
aaccgctgca atctgccggt tttcgtgtag tgatgcaaca tattatatta actcactagt   9840
attgtactat cattttggaa gaaaagaaga tcatcctcaa taatgtgtca taaatcatgc   9900
tttcatttcc tagtgatgaa gaaaaaatgt agtatatata tatatatgcc gcgtttatta   9960
tttgctaaaa tttttcattg ttactaccta ggtctgtttt gatttcctcc ctatttttgt  10020
tgtaagtttt aagtaaccaa ggacagacat aataaaaaca aggtgtgttg tatcgtatta  10080
ttgtatgtac ctatgtatgc ttacatgacc gaatggcgct aggcgctagt tacactaccc  10140
taaactgttt agcggcgccc aatctagtcg cgggtgacta actgccgcca agccattttg  10200
```

```
tggcggttca aaccgctact aaattctctc agaaccgctg caatctgccg gttttcgtgt  10260

agtgatgcaa catattatat taactcacta gtattgtact atcattttgg aagaaaagaa  10320

gatcatcctc aataatgtgt cataaatcat gctttcattt cctagtgatg aagaaaaaat  10380

gtagtatata tatatatatg ccgcgtttat tatttgctaa aatttttcat tgttactacc  10440

taggtctgtt ttgatttcct ccctattttt gttgtaagtt ttaagtaacc aaggacagac  10500

ataataaaaa caaggtgtgt tgtatcgtat tattgtatgt acctatgtat gcttacatga  10560

gtgttgtatc gtattattgt atgtacctat gtatgcttac atgagtgttg tatcgtatta  10620

ttgtatgtac ctatgtatgc ttacatga                                     10648
```

<210> SEQ ID NO 26
<211> LENGTH: 7803
<212> TYPE: DNA
<213> ORGANISM: Arachis hypogaea L. variety MJX7
<220> FEATURE:
<221> NAME/KEY: misc_feature
<222> LOCATION: (1)..(7803)
<223> OTHER INFORMATION: Genomic nucleotide sequence of LBA5b-3 from MJX7

<400> SEQUENCE: 26

```
tgggttctca ctgtccatcc attccattgc aaattcaagc atatatatgt ttccagcttc     60

atatctagct agctatagct gctaggaata taaataaaat tttttctaag atattatata    120

gtgtattttt cattatacat gttttaagtg agattaagaa aaaaatatgt gaagagcaaa    180

gatatattgt agtattacaa aagaccatca ccttttgcaa cattacttaa gaaaaaaaaa    240

aacctaagat tacctatttt tatttgatgt tgagtttagt tctgcaatct gctctgtact    300

aattatatct ttatcctaaa tataacaaag aggagtgcta aggggccagc agattttgtg    360

agttgtagcc atcaattagt catcaatagt gtatttaatg gtgtgagatt tcatctaacg    420

gtggagaatc actcattttt tttttgctgg ctaagtattg gccagatttt aataaatctg    480

ctggccccta gacttttcct ataacgaatg ctgcattctt ttttcttttt tttttctttt    540

ctcccctata atttgctaga ttatcattga tccttattat gaaattattt atttcaaaga    600

gacacatgca agagtctctt gagtttttaa gttgaaaagt gaattatgga taggtctttt    660

ttgttttata ttaaaattct attttttgtt taaaaaaatg agagtaacaa ttttataaaa    720

aaagtaaaaa ctaacatgga ctaaaagtct gattgatttg tatttgtaat tttttttattt    780

ttaatacttt gtgaaaaaat attaaataaa aaactgtaaa attatatatt ttattttatt    840

ttatttttta caaaattctt taaaaaatat gaaaatagaa ttgcaatgaa cttgtaaact    900

aatctctttt gtcctttgtt ctgatctctt attacttctt gaatataaaa aaaaaaacac    960

taactaaagt agtaattcac agaactatag tacaattatc tgcatttttt atgataatag   1020

ttcaggaaat tgcattctca tcacgtcttt cgaatactaa ttgagacata catggtggga   1080

gttttggcag aacaagaaag gggggaacat gttcaggtgc tgccatgtgt tcatgcggtt   1140

tatttttccc atgaccaact ttgctcattc taaattcctt tctttaaaca cttttttttt   1200

ttaatataat ttagaaaaaa ctttcaagta tacccgtata ttagtgtttt agtcattttt   1260

aacggttgat cttaattata tattatatat atttttgta attaagatca acggttaaaa    1320

attattaaaa caccattata cttgtacact ttaaagtttt tctataactt attttatggc   1380

aataacacat ctatgtatat atatgtcttt tcctaaccta ggaactggga agatattgta   1440

gctatctttt tttttttttt taactcttaa tagtgtgttt tgattttggc tctgctagtt   1500
```

```
agtagcaatg aagaagttct atgaagctat aatatcttca aaaaagatta tacaatagaa   1560
atagaatagt gggtgtagat aggcctacaa tgggtatgta gcagcaagat ttccaaatct   1620
agggttttga catatacatt tcctatctca atagatcttc aattaagagg ctatataatc   1680
taaatgttgc aatgtagggt ttgtagcctt gaagcacatg catatttcat ttatttgctt   1740
ctcttttatt gtattatgtt ttcttttgtt aattgaatga aggaattttt gttagatagt   1800
atatatgtac ttaaatgcaa ggctaaatat tcatatttac tttagatgaa tataaaatta   1860
aatctgatga atttctcctt gtttttgtct gaaattcaac tcatgtatag tcagactatt   1920
ttctgtatga taggtgaaca tatatatatt tttaaaaaat aatattatgt acatacaaaa   1980
attaatcacc aaattagtta tcatgtagtt agatatattt aaacatgtta catacatttt   2040
caatgtgtat ttatgagtag ttgatttgac tattgatttt tagtgtgcat ttagtgcagt   2100
tatttttcct cagtgaattg attttcattt ttttgtaatt taaatgttat atttaagcat   2160
ttaatattaa tttttgaaaa taaaaaatga acccataaga tgtgataaat cgcaaatctt   2220
gaatgcaaaa ggctagtttt tttttttttt taagccctaa ttatcatagc aagtaaacag   2280
gttaatccaa taggtttatg tcatttagtg catggtgggt caatagatcc ctgttttttc   2340
aactcatgat gtaataatac tccttatttt cacattttat gctccaactt ttgtatctca   2400
taacattcat gtagaaaata tggattaacc tgaacttgga gatttttta aaaaaaaaat   2460
catattaatt aactgtatat cttcatcata ggaatgcctg caaagttttt tgctgacatt   2520
aatgaataat ataatgttct gattgctttg ttttcaatag ctacctctta acagtatatg   2580
tttttaattt ctttgaaatg tttcagcatg gaacaaatgt tggaacgcta ccgtcaatat   2640
gtagcagatg atggtcgtat caataaatatt ggagaattcc aggtatagta aagagaatat   2700
ctataatggt atagttaagt taccatttac cgctacgata ccaacagtat ttctgtcaac   2760
ttctgctaac ttttatttat aactgtgttt aatggaagtg tttttctgga tgtgtctaat   2820
aaaaatgtct tttttatgac tgagtctaat aaaagtgttt ttataaatgt attttttgga   2880
tgtgtctttt tatacatgtg cttaaaatat aataattaat tattgttggc aataaattga   2940
cagataacct attggtaccc tatatttttc ctttaccaat atatataata tatattgact   3000
ataatacctt ttagttcttt taaaatttca ggattattta ataatatata gttttattta   3060
tttgtagtat gaaaacctat atatatttca tcaagacaac tatttggagc tagcagctag   3120
ctactcctaa taagtaataa gcatgcgata ttgatattca tagcacattt aatttgataa   3180
gaaagtgaag attattaata acacacgacc agatcaatat ataatattca tgtcatgcca   3240
tgctattaat tttttgggat tattaaagat ataactattt atgtaatttt ttcgtcaatt   3300
taagttttta gaaaaagtag tttcattaga tggtataaga gtttattggc atctagagta   3360
aataaattta ttaatgtggc tgttttatta ttatacttcc tccttcttaa attatctgat   3420
tctttttat tttttattt ttgttacatt tttagtttta agaagttatt aattaatttg   3480
tttcactata aattaaaaaa gttagaagaa tagaattatg aatggaaaga gaaattaata   3540
ttaagaacat ttttcttttt ttttgtttgt tctttacatt tttttataaa atttaatgat   3600
tattttagta attatataat taaaaagaga cagataggta agagtaacgt tttatatata   3660
gtaaaaatta aattataatg gattgtaata aaattggttt tatgctttga catgcagcaa   3720
ttggaatttg atccccaag cttggctaag aagattgaac ttcttgagct ttctcaaagg   3780
tcaatcctgt gtttaaatac taatccgttt attgctgttg ttcatattct aatactgagt   3840
attatattca ttaatatttg gtgtgccatg aaattttaat tcattgtttg aatttgttag   3900
```

```
gaagctaatg ggacagggcc tgagctcttg ttcatttgat gaactcgttg gaattgagaa   3960
tcagcttgtg tcaagcttgc aaaacattag gctcaaaaag gtcattaata attcacaaca   4020
ttatattata ttatatagat gtatatatat ataagaacaa gacgttctta atttaattaa   4080
tttaatgtac tttcaggctc agctttatag agagcatatt gaacaactac aaaataaggt   4140
acctgagctt agtttggatg caaattatac atctttaaag aattaaaaaa aattgtataa   4200
attattttaa ttaggtttca tggtggacat ctgacacatt tttatgtatt gaatccagga   4260
gaaggatttg ctcctagaga atgccaaatt aactgaaatg gtgagttacc attttctttt   4320
catgatttat agctggtttg acaaatttat ttagaaagtt atttataatt ttattgtgtt   4380
tggtaaataa aaaaataatg cgattgtatt tgtagtttta aaaagtttga agtattttga   4440
aacaaaaata ttatgtttac actaaaaatt cgttattaaa taagttttta tgtatttgta   4500
tataaataaa tatgtagttt aatttatttt taatgagttt agtagcttat ttttgtagat   4560
atttagtatg gttgattttg aaagcactta agaaaatatt ttttaaagtt agtttgtgtt   4620
tattaaaatt aaaatgtata atatatattt atatattaat aaatatttaa atttattctt   4680
atattaaaaa gtataatttt tgtctctaaa attttcaaaa tatctgtaac gtaaaatttg   4740
tttcaatttt gtttctaaca ttttaaatat atttcaatta tacctttgag ggtaggggtg   4800
gcaatcgagg aagtccgctc cgtcaaaagc ccgccatctg gtgggtctac taaatctctt   4860
tttttttttt ttatgaacta ttaaatatta aataatatat ataatttcat aactatttta   4920
ataaatttat aatttctaaa tctacaaaca ataaagtctt cataattata aatatataat   4980
aaacataatt ataaataaaa ttttttgaaa caaaatataa acattgttca aaatatataa   5040
ttaaacatct tcaaatttat aatcaatcaa atataaaaca taatccaaaa tataatttag   5100
aacatcttta attatctaca acctcttgtg tttgtaaaaa aatgtccttg accaaaaaga   5160
cgcctggttc ggtggggaag cccgctccgt cctgtcaaaa tccacggatt aagcgatgcg   5220
ggttagacag atttttaggt ttgacggttt taaattttca gtcgttcaac ccgtcttttt   5280
tagtgggtta tacggactaa tctgatgaat tttggcccgt ttgtcacctc tttttgaggg   5340
ttaacactat taatggagat gctattgtga caattatgtg ctgacatgtc actaaaacgt   5400
ggtaaaactc agctattaac atgtcagggt agtactgtca tgttatttgt tatccaacta   5460
aggaatataa ttgaaatata aaaaaccaag ttgagttggt ctagtggtga gctcattggt   5520
ttgcttaaac aagtgtttta aatcccgcct tgtgcatgca gcaacctatt ggccagtgac   5580
aaacccttaa atggagctta gtactgaggc ggattagtcc ttggcctacc gggttggagg   5640
ataccgtggc caaggatacc gtggaaaaaa aaaagaaata taaaaagtaa aattaaaact   5700
aaatgttaaa agataaaatg tgaacattga ggataaaaat agaatttatt actctattat   5760
ttttaaataa aaaatatatt aataatattc ttaaaatata tcaggtttat tgagatttat   5820
tttaatacaa taatattttt actaaaaaat tatgataaga actacatatt cttcttacaa   5880
aattataaaa aatattttaa aaatgtatca tttttaatac ataaaaatag ctttgatacc   5940
tttaaaaatt tctttagtaa tacttttaat aatttgctaa caaacatgtg attatgacaa   6000
ctaattaagt attatataga cttattagta aattatataa aaatatttta aaaagtatcc   6060
aagtgatttt tatataataa aagttatatt ttttaaaata tttttatata attttctaaa   6120
attttatagt atttataaaa agatttattt tcaataaaag atattattat attaaaatga   6180
gtctcaataa aggatattat caaaaacttt attgaatagt atattctatt tttgtcttaa   6240
```

-continued

```
atgtttatat ttattattga tctttggttt caatattact cttgatgatt tgtttaatca   6300
tatcctggac aattttacat tcctacattg agagggttgt tttcacacaa ctgtcaaggc   6360
agtatctctg ttaatagtgt tagtatttaa aaatataatt aaaaaatatt taaaatatta   6420
gaaataaaat taaaataaat taaacgtcta gtgtattttt taattttttt tttcaaattt   6480
ttagacaaaa tatatatttt atccgttact ttattgtgat caagtttcat ttgggttcaa   6540
aattctcttt ctatgtctat tatagtcaat ttaaactatg aaatttattt catcaaatgt   6600
atttattgaa agttatttat cgtttgattt atcgaatata tgtattacag ttttaagaag   6660
ttatttttca aaagagaatt ttgataaact gcgggaaaaa ataaaacctt tatccgattt   6720
tgtttttggc gaaaaattaa cgcttttggt tgggcttgtg ttccattttc gttctaacta   6780
aagaaattct ttactacatt gtaggcccaa gacctaatcc caataacgta gtgatatttt   6840
tttcaaatta ttatatttcc acatgaaaag cccatttatc cgaaggtcat aagaataact   6900
aaagtatacc caaaaaaaaa aacctaaaaa ttattccctg accaaaaaaa aaatctaaaa   6960
ttattctaaa taaagaccaa aaataaatat tcaaaagaga gagaaaatta aagaatttta   7020
cattttcgca atcacaaaga aaaaacccaa aagcgtaaac tttatcacac atgcacaaaa   7080
gaaaaaactt cgtatttgtt attcaaaaaa tgttctataa atattaaata tcattctata   7140
tgtatttgtg tatatatata tgttgtttca cacattttta acaaaataag tcactggaat   7200
agtcaattat tttttagcaa aataatgaaa ttttttatga atactaaata tatatatttt   7260
taaatatgta acaactgatt ttgtgtctat taagcatggt tattaactat tagtttatat   7320
tttttaggta ataaactttt tttgataaat aattagcaaa caaaataata gaagcacaat   7380
ggttaagggt ttgaactatt attatcaaat ttttttgtgt atagtagttt atgtattttt   7440
agctaggagt tgtaggacta agatcatgat tggctattat tagatctaaa tttatgataa   7500
gtgcaacaaa ctatttttgt tgatggcata gtgtgtgcaa agaaaaaaat cagaagagcg   7560
atgggacaaa cagagagaca caacattatc ccctagtcca agtaaccaaa gttctgttct   7620
tgtggagact gaattgttca ttggacttcc cgaatggcgc taggcgctag ttacactacc   7680
ctaaactgtt tagcggcgcc caatctagtc gcgggtgact aactgccgcc aagccatttt   7740
gtggcggttc aaaccgctac taaattctct cagaaccgct gcaatctgcc ggttttcgtg   7800
tag                                                                7803
```